United States Patent [19]
Ausubel et al.

[11] Patent Number: 6,110,709
[45] Date of Patent: Aug. 29, 2000

[54] CLEAVED AMPLIFIED MODIFIED POLYMORPHIC SEQUENCE DETECTION METHODS

[75] Inventors: Frederick M. Ausubel, Newton; Michael Mindrinos, Somerville, both of Mass.

[73] Assignee: The General Hospital Corporation, Boston, Mass.

[21] Appl. No.: 08/989,883

[22] Filed: Dec. 12, 1997

Related U.S. Application Data

[63] Continuation-in-part of application No. 08/715,484, Sep. 18, 1996, which is a continuation-in-part of application No. PCT/US95/03419, Mar. 17, 1995, and a continuation-in-part of application No. 08/210,226, Mar. 18, 1994, abandoned.

[51] Int. Cl.[7] .............. C12P 19/34; C12Q 1/68; C07H 21/04; C07H 21/00
[52] U.S. Cl. .............. 435/91.2; 435/6; 435/91.1; 536/23.1; 536/23.2; 536/24.33; 536/25.3
[58] Field of Search .............. 435/6, 91.1, 91.2; 536/23.1, 23.2, 25.3, 24.33

[56] References Cited

U.S. PATENT DOCUMENTS

| | | |
|---|---|---|
| 4,683,194 | 7/1987 | Saiki et al. . |
| 4,683,202 | 7/1987 | Mullis . |
| 4,775,619 | 10/1988 | Urdea . |
| 4,925,785 | 5/1990 | Wang et al. . |
| 5,118,605 | 6/1992 | Urdea . |
| 5,192,659 | 3/1993 | Simons . |
| 5,200,314 | 4/1993 | Urdea . |
| 5,294,534 | 3/1994 | Dattagupta et al. . |
| 5,523,225 | 6/1996 | Kraus . |
| 5,629,158 | 5/1997 | Uhlen et al. . |

FOREIGN PATENT DOCUMENTS

| | | |
|---|---|---|
| 0 327 429 | 8/1989 | European Pat. Off. . |
| WO90/06670 | 6/1990 | WIPO . |

OTHER PUBLICATIONS

Mamotte C.D.S. et al Clin Chem vol. 39 No. 1 pp. 118–121 1993.
Ugozolli L. et al GATA vol. 9 No. 4 pp. 107–112 1992.
Ho et al Gene vol. 77 pp. 51–59 1989.
Wenham et al., "Analysis of apolipoprotein E genotypes by amplification refractory mutation system," Clinical Chemistry 37:241–244, 1991.
Williams et al., "DNA polymorphisms amplified by arbitrary primers are useful as genetic markers," Nucleic Acids Research 18:6531–6535, 1990.
Fujimoto et al., "PCR–Based Restriction Fragment Length Polymerism Typing of Heliobacter Pylori," J. Clin. Microbiology 32:331–334, 1994.
Botstein et al., "Construction of a genetic linkage map in man using restriction fragment length polymorphisms," Am. J. Hum. Genet. 32:314–331, 1980.
Cha et al., "Mismatch amplification mutation assay (MAMA): Application to the c–H–ras gene," PCR Methods and Applications 2: 14–20, 1992.
Chang et al., "Multiplex mutagenically separated PCR: Diagnosis of β–thalassemia and hemoglobin variants," BioTechniques 22:520–527, 1997.
Chee et al., "Accessing genetic information with high–density DNA arrays," Science 274:610–614, 1996.
Devos and Gale, "The use of random amplified polymorphic DNA markers in wheat," Theor. Appl. Genet. 84: 567–572, 1992.
Dib et al., "A comprehensive genetic map of the human genome based on 5,264 microsatellites," Nature 380: 152–154, 1996.

(List continued on next page.)

Primary Examiner—Kenneth R. Horlick
Assistant Examiner—Jeffrey Siew
Attorney, Agent, or Firm—Clark & Elbing LLP

[57] ABSTRACT

The invention features methods for detecting polymorphic restriction sites and single nucleotide polymorphisms in nucleic acid molecules and kits for carrying out these methods.

35 Claims, 18 Drawing Sheets

OTHER PUBLICATIONS

Dietrich et al., "Mapping the mouse genome: Current status and future prospects," Proc. Natl. Acad. Sci. USA 92: 10849–10853, 1995.

Dietrich et al., "A genetic map of the mouse suitable for typing intraspecific crosses," Genetics 131:423–447, 1992.

Dietrich et al., "A comprehensive genetic map of the mouse genome," Nature 380: 149–152, 1996.

Ferrie et al., "Development, multiplexing, and application of ARMS test for common mutations in the CFTR gene," American Journal of Human Genetics 51:251–262, 1992.

Flaman et al., "A rapid PCR fidelity assay," Nucleic Acids Research 22:3259–3260, 1994.

Fodor et al., "Light–directed, spatially addressable parallel chemical synthesis," Science 251:767–773, 1991.

Gyapay et al., "The 1993–94 Genethon human genetic linkage map," Nature Genetics 7:246–249, 1994.

Guyer et al., "How is the Human Genome Project doing, and what have we learned so far?," Proc. Natl. Acad. Sci. USA 92:10841–10848, 1995.

Petruska et al., "Comparison between DNA melting thermodynamics and DNA polymerase fidelity," Proc. Natl. Acad. Sci. USA 85:6252–6256, 1988.

Rafalski and Tingey, "Genetic diagnostics in plant breeding: RAPDS, microsatellites and machines," Trends in Genetics 9:275–280, 1993.

Riedy et al., "Excess of non–parental bands in offspring from known primate pedigrees assayed using RAPD PCR," Nucleic Acids Research 20:918, 1992.

Schena et al., "Quantitative monitoring of gene expression patterns with a complementary DNA microarray," Science 270:467–470, 1995.

Schena et al., "Parallel human genome analysis: Microarray–based expression monitoring of 1000 genes," Proc. Natl. Acad. Sci. USA 93:10614–10619, 1996.

Serikawa et al., "Rat mapping using PCR–analyzed microsatellites," Genetics 131:701–721, 1992.

Southern, E. M., "DNA chips: Analysing sequence by hybridization to oligonucleotides on a large scale," Trends in Genetics 12:110–115, 1996.

Ugozzoli and Wallace, "Allele–specific polymerase chain reaction," Methods: A Companion to Methods in Enzymology 2:42–48, 1991.

Vos et al., "AFLP: A new technique for DNA fingerprinting," Nucleic Acids Research 23:4407–4414, 1995.

Pepper and Chory, "Extragenic suppressors of the arabidopsis det1 mutant identify elements of flowering–time and light–response regulatory pathways," Genetics 145:1125–1137, 1997.

Haliassos et al., "Modification of enzymatically amplified DNA for the detection of point mutations," Nucleic Acids Research 17:3606, 1989.

Goodman, M. F., "DNA polymerase fidelity: Misinsertions and mismatched extensions," pp. 17–31; in PCR Strategies, eds. Innis et al., Academic Press Inc., 1995.

Mendelman et al., "Base mispair extension kinetics: Comparison of DNA polymerase α and reverse transcriptase," The Journal of Biological Chemistry 265:2338–2346, 1990.

Perrino et al., "Extension of mismatched 3' termini of DNA is a major determinant of the infidelity of human immunodeficiency virus type 1 reverse transcriptase," Proc. Natl. Acad. Sci. USA 86:8343–8347, 1989.

Perrino and Loeb, "Differential extension of 3' mispairs is a major contribution to the high fidelity of calf thymus DNA polymerase–α," The Journal of Biological Chemistry 264:2898–2905, 1989.

Lundberg et al., "High–fidelity amplification using a thermostable DNA polymerase isolated from *Pyrococcus furiosus*," Gene 108: 1–6 1991.

Echols and Goodman, "Fidelity mechanisms in DNA replication," Annu. Rev. Biochem. 60:477–511, 1991.

Cline et al., "PCR fidelity of Pfu DNA polymerase and other thermostable DNA polymerases," Nucleic Acids Research 24:3546–3551, 1996.

Jordan and Collins, "A march of genetic maps," Nature 380:111–112, 1996.

Sarkar et al., "Characterization of polymerase chain reaction amplification of specific alleles," Analytical Chemistry 186:64–68, 1990.

Guo et al., Nucleic Acids Research 22:5456–5465 (1994).

Lisitsyn et al., Science 259:946–951 (1993).

Cox and Lehrach, "Genome Mapping: PCR Based Meiotic and Somatic Cell Hybrid Analysis," BioEssays 13:193–198 (1991).

Konieczny and Ausubel, "A Procedure for Mapping Arabidopsis Mutations Using Co–dominant Ecotype–specific PCR–based Markers," The Plant Journal 4:403–410 (1993).

Kostyu et al., "Rapid HLA–DR Oligotyping by an Enzyme–Linked Immunosorbent Assay Performed in Microtiter Trays," Human Immunology 38:148–158 (1993).

Mullis and Faloona, "Specific Synthesis of DNA in Vitro via a Polymerase–Catalyzed Chain Reaction," Methods in Enzymology 155:335–350 (1987).

Naif et al., "Early Detection of Bovine Leukemia Virus by Using an Enzyme–Linked Assay for Polymerase Chain Reaction–Amplified Proviral DNA in Experimentally Infected Cattle," J. Clin. Microbiology 30:675–679 (1992).

Reiter et al., "Global and Local Genome Mapping in Arabidopsis thaliana by using Recombinant Inbred Lines and Random Amplified Polymorphic DNAs," Proc. Natl. Acad. Sci. USA 89:1477–1481 (1992).

Saiki et al., "Genetic Analysis of Amplified DNA with Immobilized Sequence–Specific Oligonucleotide Probes," Proc. Natl. Acad. Sci. USA 86:6230–6234 (1989).

Williams et al., "Restriction Fragment Length Polymorphism Analysis of Polymerase Chain Reaction Products Amplified from Mapped Loci of Rice (Oryza sativa L..) Genomic DNA," Theor. Appl. Genet. 82:489–498 (1991).

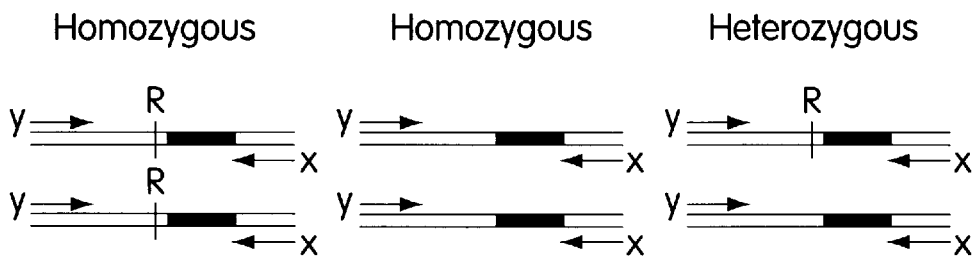

Amplify by PCR with a detectably-labeled primer (X) and a second primer (Y) tagged with the first member of a specific binding pair. Cut the products with a restriction enzyme (R). Apply the sample to the second member of the specific binding pair and measure bound label (from primer X). Hybridize filtrate to a solid support with the anchor sequence (■■■). Wash off free primer X, and measure the level of label from primer X bound to the solid support.

Material bound to second member of specific binding pair

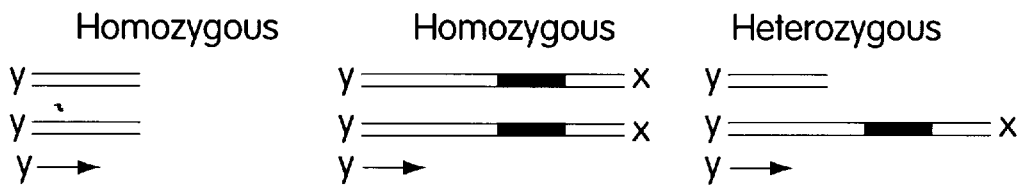

Material bound to anchor sequence

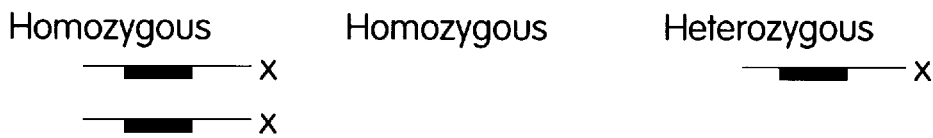

Fig. 5

| Homozygous | Homozygous | Heterozygous |

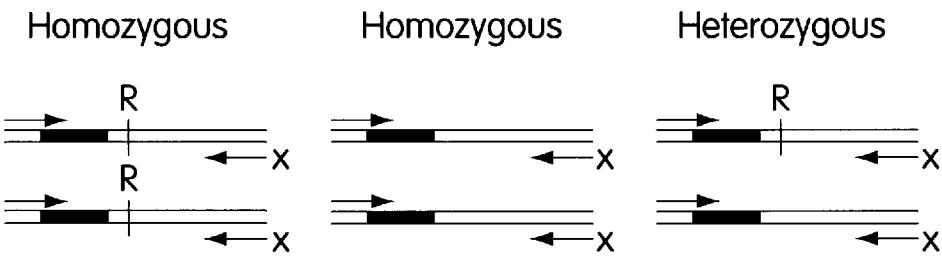

Amplify with an unlabeled primer and a tagged primer (X). Cut the products with restriction enzyme R (leaving sticky ends). Anneal and ligate to the sticky ends an oligonucleotide (Y) tagged with the first member of a specific binding pair. Apply the sample to the second member of the specific binding pair and measure bound label (from primer X). Hybridize filtrate to a solid support with the anchor sequence (▬). Wash off free primer X, and measure the level of label from primer X bound to the solid support.

Material bound to second member of specific binding pair

| Homozygous | Homozygous | Heterozygous |

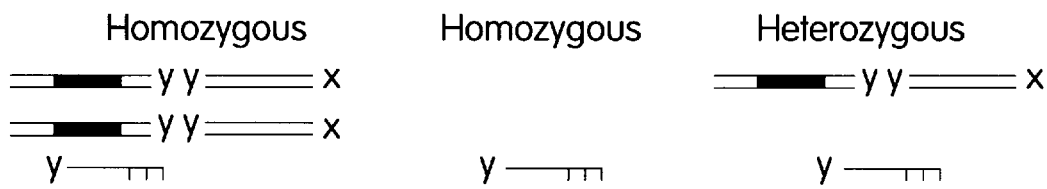

Material bound to anchor sequence

| Homozygous | Homozygous | Heterozygous |

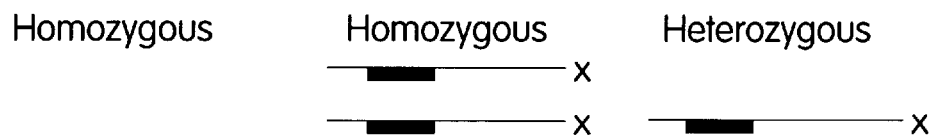

Fig. 6

PCR Reactions Used to Generate a *Hha*I Site
FIRST PCR REACTION:

```
mPr1   GTCCTTTCCGTTCTCGGTTGC ─────▶
5'...GTCCTTTCCGTTCTCGGTTC CGTA ACCCAC.........NNNNNNN 3'
3'...CAGGAAAGGCAAGAGCCAAGGCATTGGGTG.........NNNNNNN 5'
                                     ◀─────  NNNNNNN 5'  rPr1
```

SECOND PCR REACTION:

```
rPr2 ...GTCCTTTCCGTTCTCGGTTGC ─────▶
  5'    GTCCTTTCCGTTCTCGGTT GCGT AACCCACAGCCACAACACCG.....3'
  3'    CAGGAAAGGCAAGAGCCAA CGCA TTGGGTGTCGGTGTTGTGGC.....5'
                    ◀─────      GTTGGGTGTCGGTGTTGTGGC.....5' mPr2
```

FINAL PRODUCT:

```
5'...GTCCTTTCCGTTCTCGGTT GCGC AACCCACAGCCACAACACCG.....3'
3'...CAGGAAAGGCAAGAGCCAA CGCG TTGGGTGTCGGTGTTGTGGC.....5'
```

Fig. 14A

PCR Reactions Used to Generate a *Dpn*II Site
FIRST PCR REACTION:

```
mPr3   GTCCTTTCCGTTCTCGGTTCG ─────▶
5'  ...GTCCTTTCCGTTCTCGGTTC CATA ACCCAC.........NNNNNNN 3'
3'  ...CAGGAAAGGCAAGAGCCAAG GTAT TGGGTG.........NNNNNNN 5'
                                     ◀───── NNNNNNN 5' rPr3
```

SECOND PCR REACTION:

```
rPr4 ...GTCCTTTCCGTTCTCGGTTCG ─────▶
  5'    GTCCTTTCCGTTCTCGGTTC GATA ACCCACAGCCACAACACCG.....3'
  3'    CAGGAAAGGCAAGAGCCAAG CTAT TGGGTGTCGGTGTTGTGGC.....5'
              ◀───── mPr4   AGTGGGTGTCGGTGTTGTGGC.....5'
```

FINAL PRODUCT:

```
5'...GTCCTTTCCGTTCTCGGTTC GATC ACCCACAGCCACAACACCG.....3'
3'...CAGGAAAGGCAAGAGCCAAG CTAG TGGGTGTCGGTGTTGTGGC.....5'
```

Fig. 14B

*Hha*I Primer Reaction
Landsberg Allele
5 ----CCGT---- 3
3 ----GGCA---- 5
Columbia Allele
5 ----CCAT---- 3
3 ----GGTA---- 5
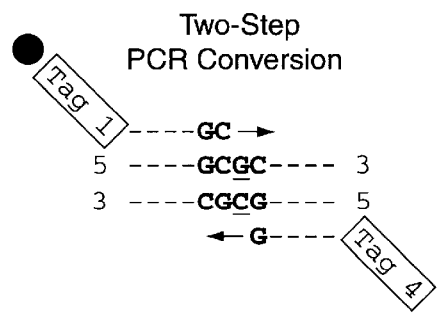
Two-Step
PCR Conversion
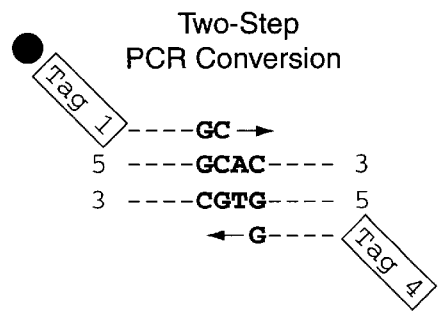
Two-Step
PCR Conversion
Labelling on
"Top" Strand
Labelling on
"Top" Strand
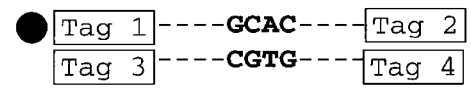
Cleavage by *Hha*I
and Hybridization
to Tags on Microarray
Non-Cleavage by *Hha*I
and Hybridization
to Tags an Microarray
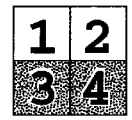
Fig. 15A

DpnII Primer Reaction
Landsberg Allele
```
5 ----CGTA---- 3
3 ----GCAT---- 5
```
Columbia Allele
```
5 ----CATA---- 3
3 ----GTAT---- 5
```
Two-Step PCR Conversion
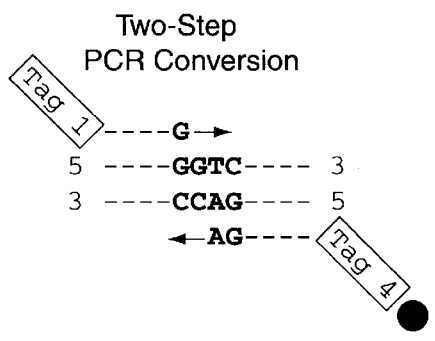
Two-Step PCR Conversion
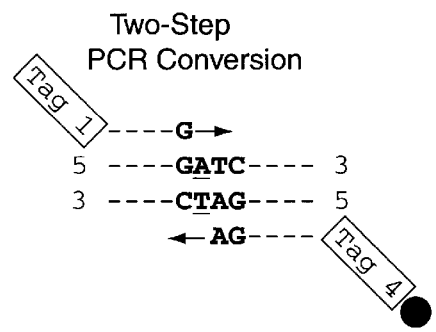
Labelling on "Bottom" Strand
Labelling on "Bottom" Strand
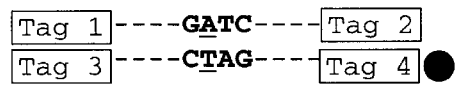
Non-Cleavage by DpnII and Hybridization to Tags an Microarray
Cleavage by DpnII and Hybridization to Tags on Microarray
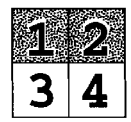
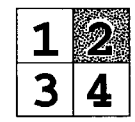
Fig. 15B

CAMPS MARKERS ARE CO-DOMINANT

| | HhaI Reaction | DpnII Reaction | HhaI + DpnII Reactions |
|---|---|---|---|
| Homozygous Landsberg | 1 2 / 3 4 | 1 2 / 3 4 | 1 2 / 3 4 |
| Homozygous Columbia | 1 2 / 3 4 | 1 2 / 3 4 | 1 2 / 3 4 |
| Heterozygous | 1 2 / 3 4 | 1 2 / 3 4 | 1 2 / 3 4 |

Fig. 16 ced Mar. 17, 1995, and U.S. Ser. No. 08/210,226,

CLEAVED AMPLIFIED MODIFIED POLYMORPHIC SEQUENCE DETECTION METHODS

This application is a continuation-in-part of U.S. Ser. No. 08/715,484, filed Sep. 18, 1996 (hereby incorporated by reference), which is a continuation-in-part of PCT/US95/03419, filed Mar. 17, 1995, and U.S. Ser. No. 08/210,226, filed Mar. 18, 1994, now abandoned.

BACKGROUND OF THE INVENTION

This invention relates to the generation and detection of genetic polymorphisms.

Genetic maps consisting primarily of restriction fragment length polymorphic (RFLP) markers are being constructed for many organisms, including man. Traditional approaches for detecting RFLPs involve Southern blot hybridization. Recently, techniques based on the polymerase chain reaction (PCR; Mullis et al., Methods Enzymol. 155:350-355, 1987) have been used in addition to, or in place of, traditional RFLP markers in genetic analysis (Cox et al., BioEssays 13:193-198, 1991). In contrast to traditional RFLP markers, PCR-generated markers can be scored using a small sample of DNA, without the use of radioactivity, and without the need for time-consuming DNA blotting procedures.

One widely used PCR-based approach involves the use of single short PCR primers of arbitrary sequence called RAPD primers (for random amplified polymorphic DNA; Reiter et al., Proc. Natl. Acad. Sci. USA 89:1477-1481, 1992; Williams et al., Theoret. Appl. Genet. 82:489-498, 1991). A second category of PCR-based markers are called SSLPs (for simple sequence length polymorphisms). The method employing SSLPs is based on amplification across tandem repeats of one or a few nucleotides known as "microsatellites." Microsatellites occur frequently and randomly in most eukaryotic genomes and display a high degree of polymorphism due to variation in the numbers of repeated units.

A third category of PCR-based markers are called AFLPs (for amplified fragment length polymorphisms). In the method employing these markers, DNA from two polymorphic strains are cleaved with one or two restriction endonucleases, and adapters are ligated to the ends of the cleaved fragments (Vos et al., Nucleic Acids Research 23: 4407-4414, 1995). The fragments are then amplified using primers complementary to the adapter(s). The primers contain short stretches of random nucleotides at their 3' ends, which result in limiting the number of amplified fragments generated.

SUMMARY OF THE INVENTION

We have developed novel PCR-based methods for detecting the presence or absence of a polymorphic restriction site or a single nucleotide polymorphism in a nucleic acid molecule involving the use of labeled PCR primers and oligonucleotides.

In a first aspect, the invention features a method for detecting the presence or absence of a single nucleotide polymorphism in a nucleic acid molecule that includes the steps of: (a) providing a nucleic acid molecule including a first strand, a second strand, and a nucleotide position suspected of including a polymorphism; (b) amplifying a segment of the nucleic acid molecule by PCR using a first primer and a second primer, wherein (i) the first primer includes a 3' region that is complementary to a first region of the first strand, the 5' end of the first region being positioned within 15 nucleotides 3' of the nucleotide position, and the 3' region of the first primer including at least one nucleotide mismatch with the first region within 15 nucleotides of the nucleotide position, (ii) the second primer includes a 3' region that is complementary to a second region of the second strand, the 5' end of the second region being positioned 3' of the nucleotide position, and (iii) the amplification generates a PCR product including at least one point mutation, relative to the sequence of the nucleic acid molecule, that forms a portion of a restriction endonuclease recognition site in the presence of a single polymorphic nucleotide in the nucleotide position; (c) labeling one end of one strand of the product of step (b) with a detectable label to generate a labeled PCR product including a labeled strand; (d) treating the labeled PCR product with a restriction endonuclease corresponding to the restriction endonuclease recognition site to generate a digestion product; (e) denaturing and contacting the digestion product with a probe that (i) is complementary to a first segment of the labeled strand that is on the opposite side of the nucleotide position from the detectable label, (ii) is not complementary to the labeled strand between the nucleotide position and the detectable label, and (iii) is immobilized to a binding element on a solid support; and (f) assaying for the detectable label bound to the binding element, wherein the absence of the label bound to the binding element indicates the presence of the single nucleotide polymorphism in the nucleic acid molecule, and the presence of the label bound to the binding element indicates the absence of the single nucleotide polymorphism in the nucleic acid molecule.

If desired, step (b) of the method may further include amplifying the PCR product by PCR using a third primer and a fourth primer, wherein (i) the third primer includes a 3' region that is complementary to a third region of the first strand, the 5' end of the third region being positioned within 15 nucleotides 3' of the nucleotide position, and the 3' region of the third primer including an additional nucleotide mismatch with the third region within 15 nucleotides of the nucleotide position, (ii) the fourth primer includes a 3' region that is complementary to a fourth region of the second strand, the 5' end of the fourth region being positioned 3' of the nucleotide position, and (iii) the amplification generates a PCR product including an additional point mutation, relative to the sequence of the nucleic acid molecule, that forms an additional portion of the restriction endonuclease recognition site in the presence of the single nucleotide polymorphism.

Alternatively, step (b) of the method may further include amplifying the PCR product by PCR using a third primer and a fourth primer, wherein (i) the third primer includes a 3' region that is complementary to a third region of the first strand, the 5' end of the third region being positioned 3' of the nucleotide position, (ii) the fourth primer includes a 3' region that is complementary to a fourth region of the second strand, the 5' end of the fourth region being positioned within 15 nucleotides 3' of the nucleotide position, and the 3' region of the fourth primer including an additional nucleotide mismatch with the fourth region within 15 nucleotides of the nucleotide position, and (iii) the amplification generates a PCR product including an additional point mutation, relative to the sequence of the nucleic acid molecule, that forms an additional portion of the restriction endonuclease recognition site in the presence of the single nucleotide polymorphism.

In a related aspect, the invention features a method for detecting the presence of a first single nucleotide polymorphism or a second single nucleotide polymorphism at a nucleotide position in a nucleic acid molecule that includes the steps of: (a) providing a first aliquot of a nucleic acid molecule that includes a first strand, a second strand, and a nucleotide position suspected of including a polymorphism; (b) amplifying a segment of the nucleic acid molecule by PCR using a first primer and a second primer, wherein (i) the first primer includes a 3' region that is complementary to a first region of the first strand, the 5' end of the first region being positioned within 15 nucleotides 3' of the nucleotide position, and the 3' region of the first primer including at least one nucleotide mismatch with the first region within 15 nucleotides of the nucleotide position, (ii) the second primer includes a 3' region that is complementary to a second region of the second strand, the 5' end of the second region being positioned 3' of the nucleotide position, and (iii) the amplification generates a first PCR product including at least one point mutation, relative to the sequence of the nucleic acid molecule, that forms a portion of a first restriction endonuclease recognition site in the presence of a first single polymorphic nucleotide in the nucleotide position; (c) labeling one end of one strand of the product of step (b) with a detectable label to generate a first labeled PCR product including a labeled strand; (d) treating the first labeled PCR product with a first restriction endonuclease corresponding to the first restriction endonuclease recognition site to generate a first digestion product; (e) denaturing and contacting the first digestion product with a first probe that (i) is complementary to a first segment of the labeled strand that is on the opposite side of the nucleotide position from the detectable label, (ii) is not complementary to the labeled strand between the nucleotide position and the detectable label, and (iii) is immobilized on a first binding element; (f) assaying for the detectable label bound to the first binding element; (g) providing a second aliquot of the nucleic acid molecule; (h) amplifying a segment of the nucleic acid molecule by PCR using a third primer and a fourth primer, wherein (i) the third primer includes a 3' region that is complementary to a first region of the first strand, the 5' end of the first region being positioned within 15 nucleotides 3' of the nucleotide position, and the 3' region of the third primer including at least one nucleotide mismatch with the first region within 15 nucleotides of the nucleotide position, (ii) the fourth primer includes a 3' region that is complementary to a second region of the second strand, the 5' end of the second region being positioned 3' of the nucleotide position, and (iii) the amplification generates a second PCR product including at least one point mutation, relative to the sequence of the nucleic acid molecule, that forms a portion of a second restriction endonuclease recognition site in the presence of a second single polymorphic nucleotide in the nucleotide position; (i) labeling one end of one strand of the product of step (h) with a detectable label to generate a second labeled PCR product including a labeled strand; (j) treating the second labeled PCR product with a second restriction endonuclease corresponding to the second restriction endonuclease recognition site to generate a second digestion product; (k) denaturing and contacting the second digestion product with a second probe that (i) is complementary to a first segment of the labeled strand that is on the opposite side of the nucleotide position from the detectable label, (ii) is not complementary to the labeled strand between the nucleotide position and the detectable label, and (iii) is immobilized on a second binding element; and (l) assaying for the detectable label bound to the second binding element, wherein (i) the absence of the label bound to the first binding element indicates the presence of the first single nucleotide polymorphism; (ii) the absence of the label bound to the second binding element indicates the presence of the second single nucleotide polymorphism; and (iii) the absence of the label bound to both of the first binding element and the second binding element indicates the presence of the first single nucleotide polymorphism and the second single nucleotide polymorphism.

In another related aspect, the invention features a kit for detecting the presence or absence of a single nucleotide polymorphism in a nucleic acid molecule that includes: (a) a first primer and a second primer flanking a nucleotide position suspected of including a polymorphism, wherein (i) the first primer includes a 3' region that is complementary to a first region of a first strand of the nucleic acid molecule, the 5' end of the first region being positioned within 15 nucleotides 3' of the nucleotide position, and the 3' region of the first primer including at least one nucleotide mismatch with the first region within 15 nucleotides of the nucleotide position, and (ii) the second primer includes a 3' region that is complementary to a second region of a second strand of the nucleic acid molecule, the 5' end of the second region being positioned 3' of the nucleotide position, wherein amplifying the nucleic acid molecule using the first primer and the second primer generates a PCR product including at least one point mutation, relative to the sequence of the nucleic acid molecule, that forms a portion of a restriction endonuclease recognition site in the presence of a single polymorphic nucleotide in the nucleotide position; and (b) a probe that either (i) is complementary to a first segment of the second strand and that is on the opposite side of the nucleotide position from the first primer and is not complementary to the second strand between the nucleotide position and the first primer, or (ii) is complementary to a first segment of the first strand that is on the opposite side of the nucleotide position from the second primer and is not complementary to the first strand between the nucleotide position and the second primer, the probe being immobilized to a binding element on a solid support.

If desired, the kit may further include a third primer and a fourth primer, wherein (i) the third primer includes a 3' region that is complementary to a third region of the first strand, the 5' end of the third region being positioned within 15 nucleotides 3' of the nucleotide position, and the 3' region of the third primer including an additional nucleotide mismatch with the third region within 15 nucleotides of the nucleotide position, and (ii) the fourth primer includes a 3' region that is complementary to a fourth region of the second strand, the 5' end of the fourth region being positioned 3' of the nucleotide position, wherein amplifying the nucleic acid molecule using the third primer and the fourth primer generates a PCR product including an additional point mutation, relative to the sequence of the nucleic acid molecule, that forms an additional portion of the restriction endonuclease recognition site in the presence of a single polymorphic nucleotide in the nucleotide position.

Alternatively, the kit may further include a third primer and a fourth primer, wherein (i) the third primer includes a 3' region that is complementary to a third region of the first strand, the 5' end of the third region being positioned 3' of the nucleotide position, and (ii) the fourth primer includes a 3' region that is complementary to a fourth region of the second strand, the 5' end of the fourth region being positioned within 15 nucleotides 3' of the nucleotide position, and the 3' region of the fourth primer including an additional nucleotide mismatch with the fourth region within 15 nucleotides of the nucleotide position, wherein amplifying the nucleic acid molecule using the third primer and the fourth primer generates a PCR product including an additional point mutation, relative to the sequence of the nucleic acid molecule, that forms an additional portion of the restriction endonuclease recognition site in the presence of a single polymorphic nucleotide in the nucleotide position.

In preferred embodiments of any of the methods or kits of the invention, any of the first primer, second primer, third primer, or fourth primer is tagged with a detectable label, and the kit may further include means for assaying the detectable label bound to the binding element.

In a preferred embodiment of any of the methods or kits described above, the labeling of the one end of the one strand of the product of step (b) is carried out by amplifying by PCR the product of step (b) using a fifth primer and a sixth primer, wherein (i) the fifth primer includes a 3' region that is complementary to a region of the first strand and that is on the same side of the nucleotide position as the first region of the first strand, (ii) the sixth primer includes a 3' region that is complementary to a region of the second strand and that is on the same side of the nucleotide position as the second region of the second strand, and (iii) either the fifth primer or the sixth primer includes a detectable label.

In preferred embodiments of any of the methods or kits described above, the first primer may further include a first tag element that is not complementary to the first strand of the nucleic acid molecule, the first tag element being positioned 5' to the 3' region of the first primer, and the first primer may further include a first universal primer binding site that is not complementary to the first strand of the nucleic acid molecule and is positioned 5' to the first tag element. In another embodiment, the labeling of the 5' end of the first strand of the product of step (b) is carried out by amplifying by PCR the product of step (b) using a seventh and an eighth primer, wherein (i) the 3' region of the seventh primer includes a region having the sequence of the first universal primer binding site, and (ii) the eighth primer includes a 3' region that is complementary to a region of the second strand that is 3' of the nucleotide position.

In other preferred embodiments of any of the methods or kits described above, the second primer further includes a second tag element that is not complementary to the second strand of the nucleic acid molecule, the second tag element being positioned 5' to the 3' region of the second primer, and the second primer may further include a second universal primer binding site that is not complementary to the second strand of the nucleic acid and is positioned 5' to the second tag element. In another embodiment, the labeling of the 5' end of the second strand of the product of step (b) is carried out by amplifying by PCR the product of step (b) using a seventh and an eighth primer, wherein (i) the 3' region of the seventh primer includes a region having the sequence of the second universal primer binding site, and (ii) the eighth primer includes a 3' region that is complementary to a region of the first strand that is 3' of the nucleotide position.

In yet other preferred embodiments of any of the methods or kits described above, the third primer further includes a first tag element that is not complementary to the first strand of the nucleic acid molecule and is positioned 5' to the 3' region of the third primer, and the third primer may further include a first universal primer binding site that is not complementary to the first strand of the nucleic acid molecule and is positioned 5' to the first tag element. In another embodiment, the labeling of the 5' end of the first strand of the product of step (b) is carried out by amplifying by PCR the product of step (b) using a seventh and an eighth primer, wherein (i) the 3' region of the seventh primer includes a region having the sequence of the first universal primer binding site, and (ii) the eighth primer includes a 3' region that is complementary to a region of the second strand that is 3' of the nucleotide position.

In other preferred embodiments of any of the methods or kits described above, the fourth primer further includes a second tag element that is not complementary to the second strand of the nucleic acid molecule and is positioned 5' to the 3' region of the fourth primer, and the fourth primer may further include a second universal primer binding site that is not complementary to the second strand of the nucleic acid molecule and is positioned 5' to the second tag element. In another embodiment, the labeling of the 5' end of the second strand of the product of step (b) is carried out by amplifying by PCR the product of step (b) using a seventh and an eighth primer, wherein (i) the 3' region of the seventh primer includes a region having the sequence of the second universal primer binding site, and (ii) the eighth primer includes a 3' region that is complementary to a region of the first strand that is 3' of the nucleotide position.

In yet other preferred embodiments of any of the methods or kits described above, the first primer may further include a first tag element that is not complementary to the first strand of the nucleic acid molecule, the first tag element being positioned 5' to the 3' region of the first primer, and the second primer may further include a second tag element that is not complementary to the second strand of the nucleic acid molecule, the second tag element being positioned 5' to the 3' region of the second primer. Upon amplification, the first tag element creates a third tag element in the complementary strand of the PCR product and the second tag element creates a fourth tag element in the complementary strand of the PCR product. In other preferred embodiments, the solid support includes four binding elements to each of which is immobilized a probe that binds one of the first tag element, the second tag element, the third tag element, or the fourth tag element, and step (f) is carried out by assaying for the detectable label bound to each of the four binding elements.

In a preferred embodiment of any of the methods or kits described above, the solid support is a chip.

The term "heterozygote," as used herein, refers to an individual with different alleles at corresponding loci on homologous chromosomes. Accordingly, the term "heterozygous," as used herein, describes an individual or strain having different allelic genes at one or more paired loci on homologous chromosomes.

The term "homozygote," as used herein, refers to an individual with the same allele at corresponding loci on homologous chromosomes. Accordingly, the term "homozygous," as used herein, describes an individual or a strain having identical allelic genes at one or more paired loci on homologous chromosomes.

The term "corresponding to a restriction endonuclease recognition site" is used herein to describe a restriction endonuclease which specifically cleaves that particular restriction endonuclease recognition site. For example, the restriction endonuclease EcoRI "corresponds" to restriction endonuclease recognition site "GAATTC." The term "tag element" is used herein to describe a nucleic acid sequence which may be included in a PCR primer and which is not complementary to a sequence in the nucleic acid molecule being amplified. Preferably, a tag element is less than 30 nucleotides long.

The term "single nucleotide polymorphism" (or "SNP") is used herein to describe any nucleotide sequence variation. Preferably, such a variation is common in a population of organisms and is inherited in a Mendelian fashion. Such alleles may or may not have associated phenotypes.

The term "universal primer" is used herein to describe a nucleotide sequence that is preferably short in length and can be readily tagged with a detectable label. Preferably, a universal primer is less than 50 nucleotides long.

The term "binding element" is used herein to describe a region of the solid support.

An advantage of certain detection methods of the present invention over many other methods used to detect genetic polymorphisms is that gel electrophoresis is not required in the analysis. Thus, the methods of the present invention are readily adaptable for automation, allowing large numbers of samples to be processed in relatively short periods of time, at lower costs. In certain of the embodiments, detection of an array of samples is carried out simultaneously on a solid support, such as a glass slide or a microchip, further reducing processing time and cost. Detection of signals on arrays can be carried out quantitatively or qualitatively. In addition, in several variations of the methods of the invention (see, e.g., Examples III and IV below), internal controls are provided, thus controlling for variability detected by different practitioners. Furthermore, in several of the variations of the methods of the invention (see Examples III–VIII and XII–XIV below), an oligonucleotide probe hybridizing to a sequence in the PCR product internal to the primers is used to purify the products, thus allowing a reduction in background problems associated with PCR amplification.

Those detection methods of the invention utilizing gel electrophoresis are also advantageous because they provide a rapid and inexpensive approach to the identification of large numbers of PCR-based genetic and RFLP markers.

The method of the invention useful for cloning genetic polymorphisms also represents an improvement over current methods. Because the process of selecting out a tagged (e.g., biotinylated) DNA having a polymorphism involves a specific hybridization step, candidate DNA from any source may be utilized. For example, DNA from random clones, CDNA libraries, YAC libraries, or any other DNA collection may be screened; pure preparations of genomic DNAs are not required. Moreover, like other methods of the invention, this cloning procedure is rapid and inexpensive.

Another method of the invention, termed Cleaved Amplified Modified Polymorphic Sequences, or "CAMPS" (see Example XV below), has the advantage of being useful for rapidly detecting a single nucleotide polymorphism in a nucleic acid molecule. This rapid detection method is readily applicable to high through-put assays and may be used to determine the heterozygosity or homozygosity for a particular allele of a nucleic acid molecule.

All methods of the invention are useful in clinical diagnostic testing, genomic mapping, positional cloning of genes defined by mutation (such as those that cause inherited disease in humans or resistance to pathogens in crop plants), DNA fingerprinting (e.g., for forensic analysis and paternity testing), crop and livestock breeding programs, and other related applications.

In one particular example, the detection methods of the invention are useful for bacterial typing utilizing known conserved polymorphic sequences diagnostic of the bacterium. In one application, this approach is useful for distinguishing one bacterium from another (e.g., for the identification of Salmonella in a food sample); polymorphism-containing sequences preferred for this approach include those present in conserved ribosomal RNA genes. In another application, this approach is useful for screening bacteria (e.g., clinical isolates) for antibiotic resistance; in this case, known polymorphic restriction sites within the antibiotic resistance marker are utilized. The instant methods of bacterial typing decrease false positive results frequently obtained using current PCRbased techniques.

Other features and advantages of the invention will be apparent from the following detailed description, the drawings, and the claims.

BRIEF DESCRIPTION OF THE DRAWINGS

FIG. 5 is a schematic of a RFLP detection method involving the use of a first PCR primer tagged with a detectable label (X) and a second PCR primer tagged with the first member of a first specific binding pair (Y). After amplification by PCR, the products are digested with the restriction enzyme (R) corresponding to the polymorphic restriction site, and are contacted with the second member of the first specific binding pair immobilized on a first solid support. The filtrate is then bound to a solid support with the anchor sequence (or contacted with an oligonucleotide complementary to the X strand between the restriction site (R) and the label (X), the oligonucleotide being tagged with the first member of a second specific binding pair, and then contacted with the second member of the second specific binding pair immobilized on a second solid support), and the levels of the detectable label bound to the first solid support and the anchor sequence (or second solid support) are determined.

FIG. 6 is a schematic of a RFLP detection method involving the use of a first unlabeled PCR primer and a second PCR primer tagged with a detectable label (X). After amplification by PCR, the products are digested with the restriction enzyme (R) corresponding to the polymorphic restriction site, and contacted with an oligonucleotide complementary to the single-stranded ends generated in the digestion, the oligonucleotide being tagged with the first member of a specific binding pair. The products are then contacted with the second member of the first specific binding pair, bound to a first solid support. The filtrate is then bound to a solid support with the anchor sequence (or contacted with an oligonucleotide complementary to the X strand, the oligonucleotide being tagged with the first member of a second specific binding pair, and then contacted with the second member of the second specific binding pair immobilized on a second solid support), and the levels of the detectable label bound to the first solid support and the anchor sequence (or second solid support) are determined.

FIG. 14A is a schematic of a method involving two separate PCR amplifications used to generate a HhaI site from an SNP (shown here as the underlined bold GC base pair).

FIG. 14B is a schematic of a method involving two separate PCR amplifications used to generate a DpnII site from an SNP (shown here as the underlined bold AT base pair).

FIG. 15A is a schematic of a method used to identify the presence of a Landsberg allele using labeling, exposure to the restriction endonuclease, HhaI, and hybridization to tag elements on a microarray. The Landsberg SNP is shown on the left of the figure as the underlined bold GC base pair.

FIG. 15B is a schematic of a method used to identify the presence of a Columbia allele using labeling, exposure to the restriction endonuclease, DpnII, and hybridization to tag elements on a microarray. The Columbia SNP is shown on the right of the figure as the underlined bold AT base pair.

FIG. 16 is a schematic demonstrating the co-dominant nature of CAMPS markers. Using the CAMPS method with two different restriction endonucleases, HhaI and DpnII (corresponding to the Landsberg and Columbia SNPs, respectively), an individual is identified as homozygous Landsberg, homozygous Columbia, or heterozygous for both alleles.

DETAILED DESCRIPTION

Figure 1:
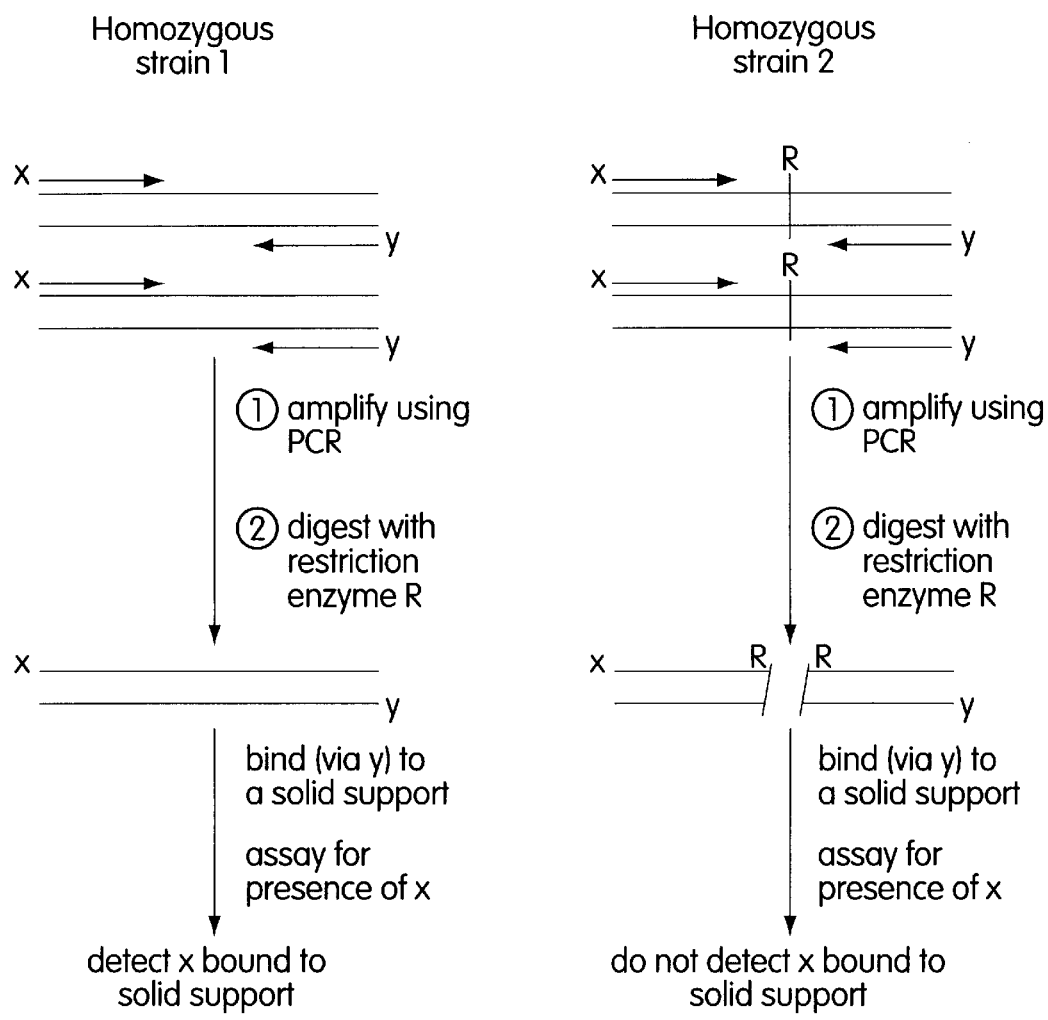
FIG. 1 is a schematic of a RFLP detection method involving the use of a first PCR primer tagged with a detectable label (X) and a second PCR primer tagged with the first member of a specific binding pair (Y). After amplification by PCR, the products are digested with the restriction endonuclease (R) corresponding to the polymorphic restriction site, contacted with the second member of the specific binding pair immobilized on a solid support, and the level of the detectable label (X) bound to the solid support is determined.

The present invention provides several methods for detecting Cleaved Amplified Polymorphic Sequences (CAPS; Konieczny et al., The Plant Journal 4(2):403–410, 1993) and for detecting Single Nucleotide Polymorphisms (SNPs) with a novel method we have termed "CAMPS" for Cleaved Amplified Modified Polymorphic Sequences. In the CAPS method, a nucleic acid containing a polymorphic restriction site is amplified using primers flanking the restriction site. The resulting PCR product is digested with the restriction endonuclease corresponding to the polymorphic restriction site, and the digested products are analyzed by gel electrophoresis.

In the CAMPS method, a nucleic acid molecule containing a single nucleotide polymorphism is mutagenized during PCR amplification to create a restriction endonuclease recognition site which includes the single nucleotide polymorphism. The resulting PCR product is digested with the corresponding restriction endonuclease, and the restriction endonuclease-treated products are analyzed for cleavage in a rapid high through-put assay.

The detection methods of the present invention vary greatly from one another in detail, however they share three central features: (1) a nucleic acid molecule containing a polymorphic restriction site is amplified by PCR using the same or differently labeled primers flanking the polymorphic restriction site, (2) the resulting PCR product is digested with the restriction endonuclease corresponding to the polymorphic restriction site (which will cleave the DNA amplified from some individuals but not cleave the DNA amplified from other individuals, depending on the presence of the polymorphism), and (3) the resulting digestion products are analyzed by detection of the labels they contain, and/or labels attached to oligonucleotides complementary to the digestion products, in order to determine the identity of the polymorphic restriction site. The methods of the invention allow rapid and efficient analyses of a large number of samples.

The nucleic acid sample containing the polymorphic restriction site being analyzed can be obtained from any source, e.g., a tissue homogenate, blood, amniotic fluid, chorionic villus samples, and a bacterial culture; and can be obtained from these sources using standard methods. Only a minute quantity of nucleic acid is required, and can be DNA or RNA (in the case of RNA, a reverse transcription step is required before the PCR step). The PCR methods used in the methods of the present invention are carried out using standard methods (see, e.g., Ausubel et al., Current Protocols in Molecular Biology, John Wiley and Sons, New York, 1989; Erlich, PCR Technology, Stockton Press, New York, 1989; Innis et al., PCR Protocols: A Guide to Methods and Applications, Academic Press, Harcourt Brace Javanovich, New York, 1990; Sambrook et al., Molecular Cloning: A Laboratory Manual, Cold Spring Harbor Laboratory Press, Cold Spring Harbor, N.Y., 1989). Restriction enzyme digestion is also carried out by standard methods using any of a number of available restriction endonucleases (see, e.g., Ausubel et al., supra; New England Biolabs, Beverly, Mass.).

The primers and oligonucleotides used in the methods of the present invention are preferably DNA, and can be synthesized using standard techniques and, when appropriate, detectably labeled using standard methods (Ausubel et al., supra). Detectable labels that can be used to tag the primers and oligonucleotides used in the methods of the invention include, but are not limited to, digoxigenin, fluorescent labels (e.g., fluorescein and rhodamine), enzymes (e.g., horseradish peroxidase and alkaline phosphatase), biotin (which can be detected by anti-biotin specific antibodies or enzyme-conjugated avidin derivatives), radioactive labels (e.g., $^{32}P$ and $^{125}I$), calorimetric reagents, and chemiluminescent reagents. The labels used in the methods of the invention are detected using standard methods.

The specific binding pairs useful in the methods of the invention include, but are not limited to, avidin-biotin, streptavidin-biotin, hybridizing nucleic acid pairs, interacting protein pairs, antibody-antigen pairs, reagents containing chemically reactive groups (e.g., reactive amino groups), and nucleic acid sequence-nucleic acid binding protein pairs.

The solid supports useful in the methods of the invention include, but are not limited to, agarose, acrylamide, and polystyrene beads; polystyrene microtiter plates (for use in, e.g., ELISA); and nylon and nitrocellulose membranes (for use in, e.g., dot or slot blot assays).

Some methods of the invention employ solid supports containing arrays of nucleic acid probes. In these cases, solid supports made of materials such as glass (e.g., glass plates), silicon or silicon-glass (e.g., microchips), or gold (e.g., gold plates) can be used. Methods for attaching nucleic acid probes to precise regions on such solid surfaces, e.g., photolithographic methods, are well known in the art, and can be used to make solid supports for use in the invention. (For example, see, Schena et al., Science 270:467–470, 1995; Kozal et al., Nature Medicine 2(7):753–759, 1996; Cheng et al., Nucleic Acids Research 24(2):380–385, 1996; Lipshutz et al., BioTechniques 19(3):442–447, 1995; Pease et al., Proc. Natl. Acad. Sci. USA 91:5022–5026, 1994; Fodor et al., Nature 364:555–556, 1993; Pirrung et al., U.S. Pat. No. 5,143,854; and Fodor et al., WO 92/10092.)

The methods of the invention can be facilitated by the use of kits which contain the reagents required for carrying out the assays. The kits can contain reagents for carrying out the analysis of a single polymorphic restriction site (for use in, e.g., diagnostic methods) or multiple polymorphic restriction sites (for use in, e.g., genomic mapping). When multiple samples are analyzed, multiple sets of the appropriate primers and oligonucleotides are provided in the kit. In addition to the primers and oligonucleotides required for carrying out the various methods, the kits may contain the enzymes used in the methods, and the reagents for detecting the labels, e.g., the substrates for enzyme labels, etc. The kits can also contain solid substrates for used in carrying out the method of the invention. For example, the kits can contain solid substrates, such as glass plates or silicon or glass microchips, containing arrays of nucleic acid probes.

As discussed above, the invention provides methods and kits for generating and detecting the presence or absence of a polymorphic restriction site in a nucleic acid molecule. Examples I–IX and XII–XIV describe eight variations of the methods of the invention. Example X describes a preferred use for the methods of the invention. Example XI describes a preferred method for cloning polymorphic restriction fragments. Example XV describes a method for rapidly detecting the presence or absence of a single nucleotide polymorphism in a nucleic acid molecule.

The following examples are meant to illustrate, but not limit, the methods of the present invention. Other suitable modifications and adaptations of the variety of conditions and parameters of molecular biology which are obvious to those skilled in the art are within the spirit and scope of the present invention.

EXAMPLES

Example I.

In this method, the nucleic acid containing the polymorphism is amplified by PCR using a first and a second primer flanking the polymorphic restriction site, the first primer being tagged with the first member of a specific binding pair, the second primer being tagged with a detectable label. The resulting PCR product is digested with the restriction endonuclease corresponding to the polymorphic restriction site and the digested products are contacted with the second member of the specific binding pair, immobilized on a solid support. The level of the detectable label bound to the solid support is then measured. The presence of the detectable label bound to the solid support is an indication of the absence of the polymorphic restriction site in the nucleic acid, while the absence of the detectable label bound to the solid support is an indication of the presence of the polymorphic restriction site in the nucleic acid. An embodiment of this method is shown in FIG. 1.

Example II.

Figure 2:
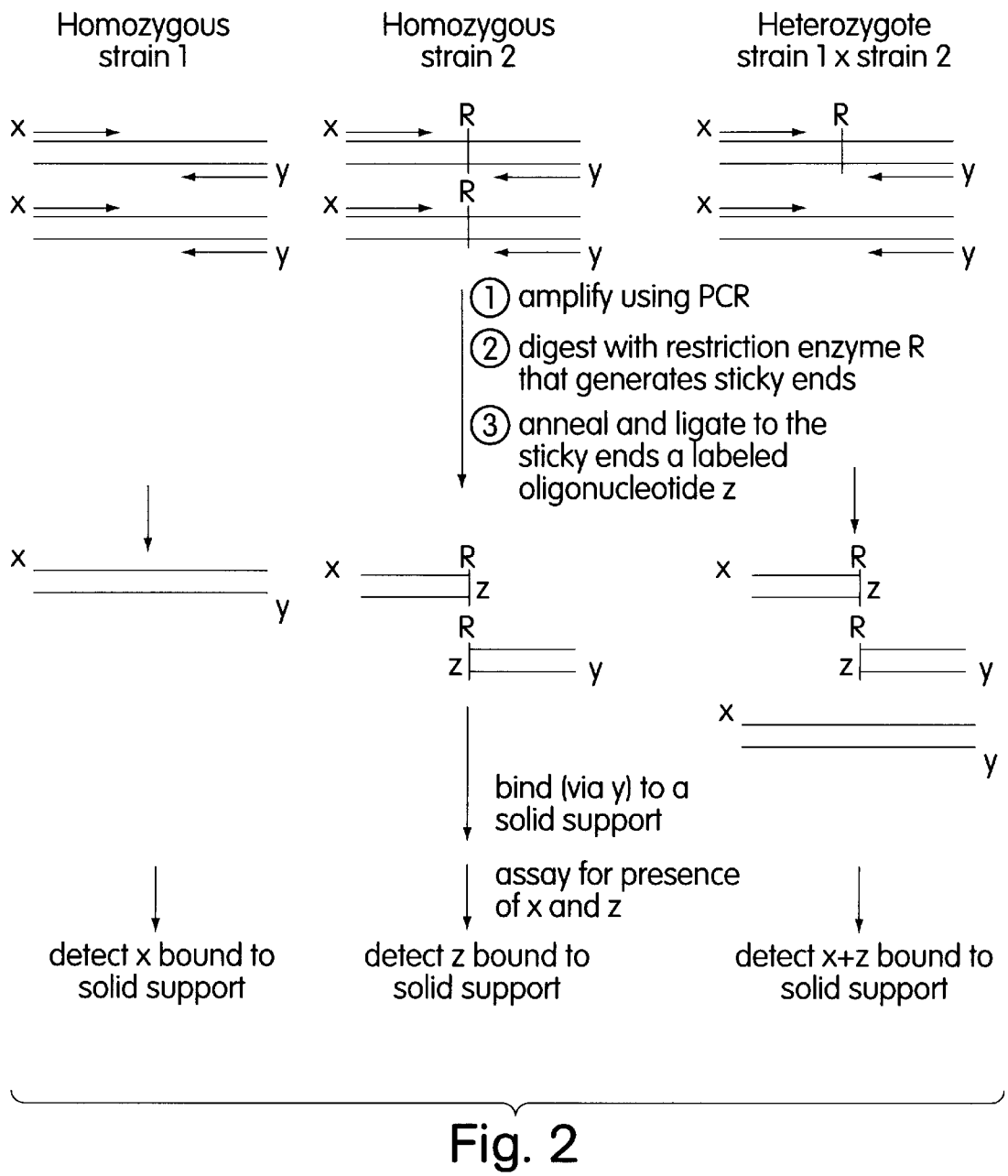
FIG. 2 is a schematic of a RFLP detection method involving the use of a first PCR primer tagged with a first detectable label (X) and a second PCR primer tagged with the first member of a specific binding pair (Y). After amplification by PCR, the products are digested with the restriction endonuclease (R) corresponding to the polymorphic restriction site, and an oligonucleotide tagged with a second detectable label (Z) is annealed and ligated to the single-stranded ends generated in the digestion. The reaction is then contacted with the second member of the specific binding pair bound to a solid support, and the levels of the first and second detectable labels (X and Z) bound to the solid support are determined.

This method is identical to that described in Example I, with the added step of annealing and ligating to the single-stranded ends generated in the digestion reaction, an oligonucleotide tagged with a second detectable label. After applying the reaction to the second member of the specific binding pair, the levels of both the first and the second detectable labels bound to the solid support are determined. The presence of only the first detectable label bound to the solid support is an indication of a homozygote lacking the polymorphic restriction site, the presence of only the second detectable label bound to the solid support is an indication of a homozygote containing the polymorphic restriction site, and the presence of both the first and the second detectable labels bound to the solid support is an indication of a heterozygote. An embodiment of this method is shown in FIG. 2.

Figure 12:
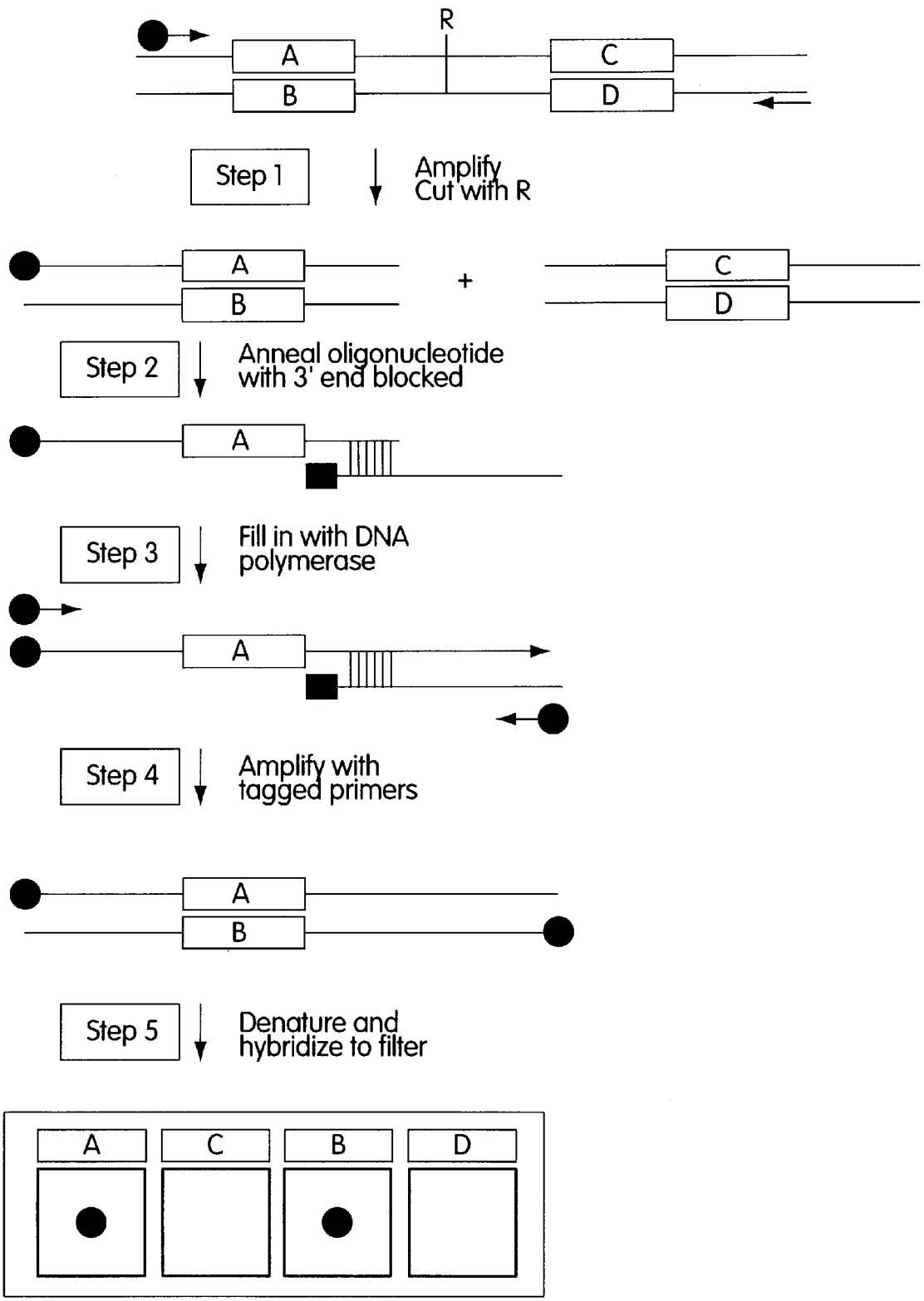
FIG. 12 is a schematic of a method for detecting a cleaved end of a CAPS marker.

In addition to labeling the cleaved ends of the CAPS products by annealing and ligating an oligonucleotide to the sticky ends generated by the cleavage, as is described above, and, e.g., in Examples VI and VIII, the cleaved ends can be labeled by using a method described in further detail below in Example XIV. Briefly, in this method, the denatured product is contacted with an oligonucleotide to generate a first reaction product. The oligonucleotide contains a 3' portion that hybridizes to a first region in the first strand that flanks the polymorphic restriction site on the side of the polymorphic restriction site containing a sequence corresponding to the first primer. The 3' end of the oligonucleotide is blocked by, e.g., a di-deoxynucleotide, so that it cannot serve as a primer for DNA polymerase. The oligonucleotide contains a 5' portion that does not hybridize to a second region in the first strand that flanks the polymorphic restriction site on the side of the polymorphic restriction site containing a sequence that is complementary to the second primer. The use of such an oligonucleotide to label a cleaved end of a CAPS marker is illustrated in FIG. 12. This method can also be applied to the CAPS detection techniques of, for example, Examples VI and VIII.

Example III.

In this method, the nucleic acid is amplified using a first and a second primer flanking the polymorphic restriction site, the first primer being tagged with a detectable label, the second primer being unlabeled. A portion of the PCR reaction is digested with the restriction endonuclease corresponding to the polymorphic restriction site, while another portion is left undigested. Both the digested and undigested portions are then denatured, and contacted with an oligonucleotide tagged with the first member of a specific binding pair. The oligonucleotide is complementary to a sequence in the strand of the PCR product containing the detectable label, the sequence being between the polymorphic restriction site and the sequence complementary to the second primer.

Figure 3:
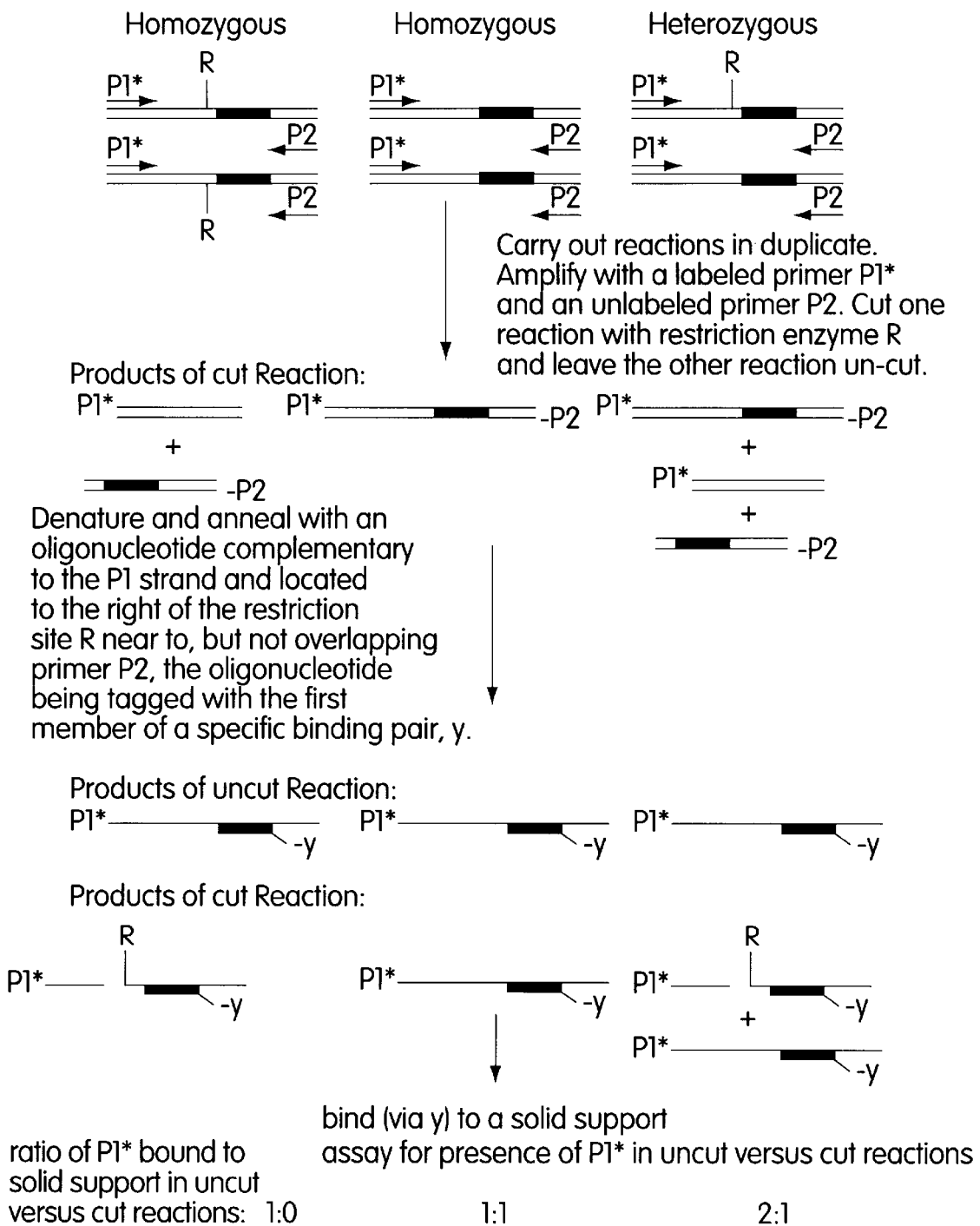
FIG. 3 is a schematic of a RFLP detection method involving the use of a first PCR primer tagged with a detectable label (P1) and a second unlabeled PCR primer (P2). After amplification by PCR, half of the reaction (or one of the identical reactions if carried out in duplicate) is digested with the restriction endonuclease (R) corresponding to the polymorphic restriction site. Both digested and undigested reactions are then denatured and contacted with an oligonucleotide tagged with the first member of a specific binding pair, the oligonucleotide being complementary to the P1 strand and located to the right of the restriction site (R) near to, but not overlapping, primer P2. The reactions are then contacted with the second member of the specific binding pair immobilized on a solid support, and the levels of P1 in digested versus undigested reactions are compared.

The reaction is then contacted with the second member of the specific binding pair, immobilized on a solid support, and the ratio of the levels of the detectable label bound to the solid support between undigested and digested samples is determined. A ratio of 1:0 between equivalent portions of undigested and digested samples is an indication of a homozygote containing the polymorphic restriction site, a ratio of 1:1 between equivalent portions of undigested and digested samples is an indication of a homozygote lacking the polymorphic restriction site, and a ratio of 2:1 between equivalent portions of undigested and digested samples is an indication of a heterozygote. While the sample volumes used for detection and comparison need not be equivalent, the appropriate calculations must be carried out to account for this adjustment prior to determining the ratio of detectable label in digested and undigested samples. An embodiment of this method is shown in FIG. 3.

Example IV.

In this method, the nucleic acid is amplified by PCR using a first primer and a second primer flanking the polymorphic restriction site, the first primer being tagged with a first detectable label, and the second primer being tagged with a second detectable label.

The PCR product is digested with the restriction endonuclease corresponding to the polymorphic restriction site, denatured, and contacting with a first and a second oligonucleotide. The first oligonucleotide is complementary to a first sequence in the strand of the PCR product containing the first detectable label, the first sequence being between the polymorphic restriction site and the sequence corresponding to the first primer. The first oligonucleotide is tagged with the first member of a first specific binding pair. The second oligonucleotide is complementary to a second sequence in the strand of the PCR product containing the second detectable label. The second sequence is on the same side of the polymorphic restriction site as the first sequence, and is not contained within, or complementary to, either the first or the second primer. The second oligonucleotide is tagged with the first member of a second specific binding pair.

A first portion of the reaction is then contacted with the second member of the first specific binding pair, immobilized on a first solid support, while a second portion of the reaction is contacted with the second member of the second specific binding pair, immobilized on a second solid support. The ratio of the levels of the first and second detectable labels bound to the first and second solid supports is then determined. A ratio of 1:0 between equivalent amounts of the first and second portions is an indication of a homozygote containing the polymorphic restriction site, a ratio of 1:1 between equivalent amounts of the first and second portions is an indication of a homozygote lacking the polymorphic restriction site, and a ratio of 2:1 between equivalent amounts of the first and second portions is an indication of a heterozygote.

Figure 4:
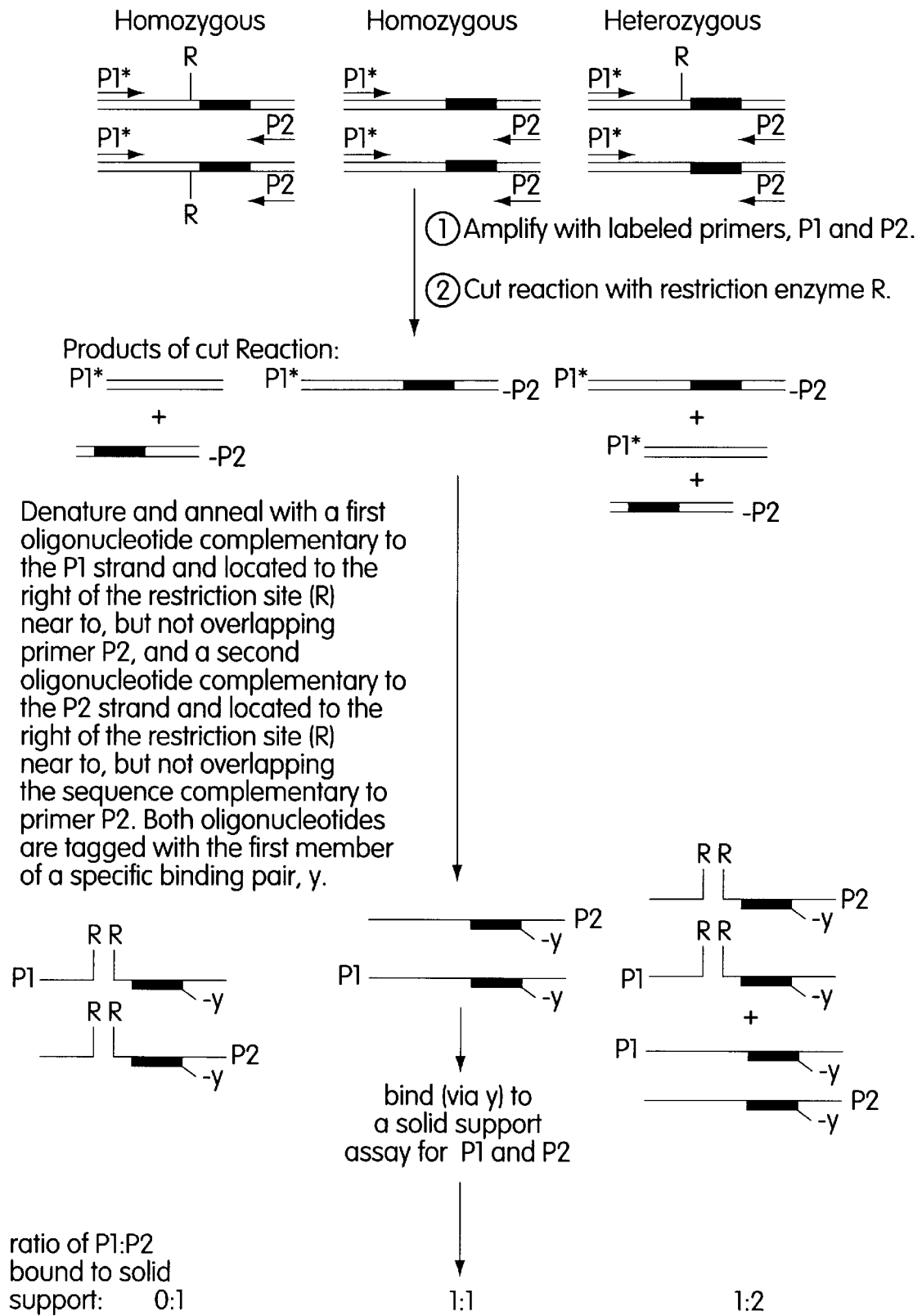
FIG. 4 is a schematic of a RFLP detection method involving the use of a first PCR primer tagged with a first detectable label (P1) and a second PCR primer tagged with a second detectable label (P2). After amplification by PCR, the products are digested with the restriction endonuclease (R) corresponding to the polymorphic restriction site, denatured, and contacted with a first oligonucleotide complementary to the PI strand and located to the right of the restriction site (R) near to, but not overlapping primer P2, and a second oligonucleotide complementary to the P2 strand and located to the right of the restriction site (R) near to, but not overlapping the sequence complementary to primer P2. Both the first and second oligonucleotides are tagged with the first member of a specific binding pair (Y). The reactions are then contacted with the second member of the specific binding pair immobilized on a solid support, and the ratio of P1 to P2 bound to the solid support is determined.

In the case where the first sequence (to which the first oligonucleotide is complementary) in the strand containing the first detectable label is between the polymorphic restriction site and the sequence complementary to the second primer, the ratios differ, as follows. The ratio of the levels of the first and second detectable labels bound to the first and second solid supports is 0:1 between equivalent amounts of the first and second portions in the case of a homozygote containing the polymorphic restriction site. The ratio is 1:1 between equivalent amounts of the first and second portions in the case of a homozygote lacking the polymorphic restriction site, and the ratio is 1:2 between equivalent amounts of the first and second portions in the case of a heterozygote. An embodiment of this method is shown in FIG. 4.

Example V.

In this method, the nucleic acid is amplified by PCR using a first and a second primer flanking the polymorphic restriction site, the first primer being tagged with the first member of a first specific binding pair, the second primer being tagged with a detectable label. The PCR product is digested with the restriction endonuclease corresponding to the polymorphic restriction site, and the reaction is then contacted with the second member of the first specific binding pair, immobilized on a first solid support.

The material not bound to the first solid support is denatured and contacted with an oligonucleotide complementary to a sequence in the strand of the PCR product containing the detectable label. The sequence is between the polymorphic restriction site and the sequence corresponding to the second primer, and the oligonucleotide is tagged with the first member of a second specific binding pair. The reaction is then contacted with the second member of the second specific binding pair, immobilized on a second solid support, and the ratio of the level of the detectable label bound to the first solid support compared to the level of the detectable label bound to the second solid support is determined. A ratio of 0:1 is an indication of a homozygote containing the polymorphic restriction site, a ratio of 1:0 is an indication of a homozygote lacking the polymorphic restriction site, and a ratio of 1:1 is an indication of a heterozygote. These ratios are correct in cases where the total amount of the material not bound to the first solid support is used in the following steps, and should be adjusted accordingly, if a different amount of the material is used. An embodiment of this method is shown in FIG. 5.

Example VI.

In this method, the nucleic acid is amplified by PCR using a first and a second primer flanking the polymorphic restriction site, the first primer being tagged with a detectable label, the second primer being unlabeled. The PCR product is digested with the restriction endonuclease corresponding to the polymorphic restriction site, and a first oligonucleotide tagged with the first member of a first specific binding pair is annealed and ligated to the single-stranded ends generated in the digestion reaction. The reaction is then contacted with the second member of the first specific binding pair, immobilized on a first solid support.

The material not bound to the first solid support is denatured, and contacted with a second oligonucleotide complementary to a sequence in the strand of the PCR product containing the detectable label, the sequence being between the polymorphic restriction site and either the sequence corresponding to the first primer or the sequence complementary to the second primer. The second oligonucleotide is tagged with the first member of a second specific binding pair. The reaction is then contacted with the second member of the second specific binding pair, immobilized on a second solid support, and the ratio of the level of the detectable label bound to the first solid support compared to the level of the detectable label bound to the second solid support is determined. A ratio of 1:0 is an indication of a homozygote containing the polymorphic restriction site, a ratio of 0:1 is an indication of a homozygote lacking the polymorphic restriction site, and a ratio of 1:1 is an indication of a heterozygote. These ratios are correct in cases where the total amount of the material not bound to the first solid support is used in the following steps, and should be adjusted accordingly, if a different amount of the material is used. An embodiment of this method is shown in FIG. 6.

Example VII.

In this method, the nucleic acid is amplified by PCR using a first and a second primer flanking the polymorphic restriction site, the first primer being tagged with the first member of a first specific binding pair, the second primer being tagged with a detectable label. The PCR product is digested with the restriction endonuclease corresponding to the polymorphic restriction site, and contacted with the second member of the first specific binding pair, immobilized on a first solid support.

The material not bound to the first solid support is denatured and contacted with an oligonucleotide complementary to a sequence in the strand of the PCR product containing the detectable label. The sequence is between the polymorphic restriction site and the sequence corresponding to the second primer, and the oligonucleotide is immobilized on a second solid support (e.g., a nylon or nitrocellulose membrane).

The ratio of the level of detectable label bound to the first solid support to the level of detectable label bound to the second solid support is then determined. A ratio of 0:1 is an indication of a homozygote containing the polymorphic restriction site, a ratio of 1:0 is an indication of a homozygote lacking the polymorphic restriction site, and a ratio of 1:1 is an indication of a heterozygote. These ratios are correct in cases where the total amount of the material not bound to the first solid support is used in the following steps, and should be adjusted accordingly, if a different amount of the material is used. An embodiment of this method is shown in FIG. 5.

Example VIII.

In this method, the nucleic acid is amplified by PCR using a first and a second primer flanking the polymorphic restriction site, the first primer being tagged with a detectable label, the second primer being unlabeled. The PCR product is digested with the restriction endonuclease corresponding to the polymorphic restriction site, and a first oligonucleotide tagged with the first member of a first specific binding pair is annealed and ligated to the single-stranded ends generated in the digestion reaction. The reaction is contacted with the second member of the first specific binding pair, immobilized on a first solid support. The material not bound to the first solid support is denatured, and contacted with a second oligonucleotide complementary to a sequence in the strand of the PCR product containing the detectable label. The sequence is between the polymorphic restriction site and either the sequence corresponding to the first primer or the sequence complementary to the second primer, and the second oligonucleotide is immobilized on a second solid support (e.g., a nylon or nitrocellulose membrane).

The ratio of the level of the detectable label bound to the first solid support to the level of the detectable label bound to the second solid support is then determined. A ratio of 1:0 is an indication of a homozygote containing the polymorphic restriction site, a ratio of 0:1 is an indication of a homozygote lacking the polymorphic restriction site, and a ratio of 1:1 is an indication of a heterozygote. These ratios are correct in cases where the total amount of the material not bound to the first solid support is used in the following steps, and should be adjusted accordingly, if a different amount of the material is used. An embodiment of this method is shown in FIG. 6.

PCR primers containing nucleic acid tags on their 5' ends can also be used in the methods of the invention. These primers can be used in pairs, or in combination with untagged primers, in the initial cycles of PCR, followed by the addition of a "universal primer(s)" complementary to the nucleic acid tags in the first primers, and contain detectable labels (e.g., biotin, fluorescent, or ELISA tags). The use of nucleic acid tagged primers in the early rounds of PCR is a cost-effective measure, as only one set of primers, the universal primers, which can be used in the analysis of many different polymorphic sites, need to be detectably labeled. The sets of primers specific for individual polymorphic restriction sites do not have to be tagged with detectable labels, but rather need only to be complementary to the universal primers in their 5' ends.

Example IX.

Figure 7:
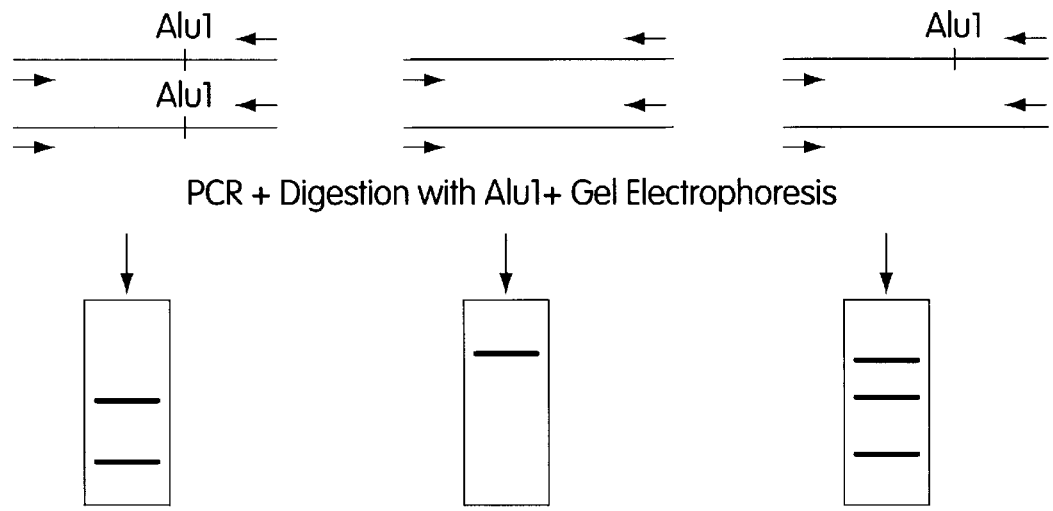
FIG. 7 is a schematic of a RFLP detection method involving the use of PCR primers flanking the polymorphic restriction site (the "Alu I" site). Following PCR amplification, the reaction products are digested with the restriction endonuclease corresponding to the polymorphic restriction site (Alu I), and the fragments are run on an agarose gel. The separated fragments are detected as an indication of the presence or absence of the polymorphic marker.

In another method of the invention, the nucleic acid is amplified by PCR using a first and a second primer flanking the polymorphic restriction site. The PCR product is digested with the restriction endonuclease corresponding to the polymorphic restriction site, and, as shown in FIG. 7, the digestion products are run on a gel (preferably an agarose gel). To simplify the gel reading, the first and second primers are preferably designed to generate a PCR product that is easily resolvable on an agarose gel (e.g., preferably larger than 100 base pairs and smaller than 1000 base pairs), and the polymorphic restriction site is preferably located at an asymmetric position within the amplified fragment. Using this technique, short gel runs can be used for analysis, and the cleaved products are easily detected. In the particular example shown in FIG. 8, primers are designed to produce PCR amplified products of 300 base pairs, and cleavage at the RFLP site yields products of 200 base pairs and 100 base pairs.

Figure 8:
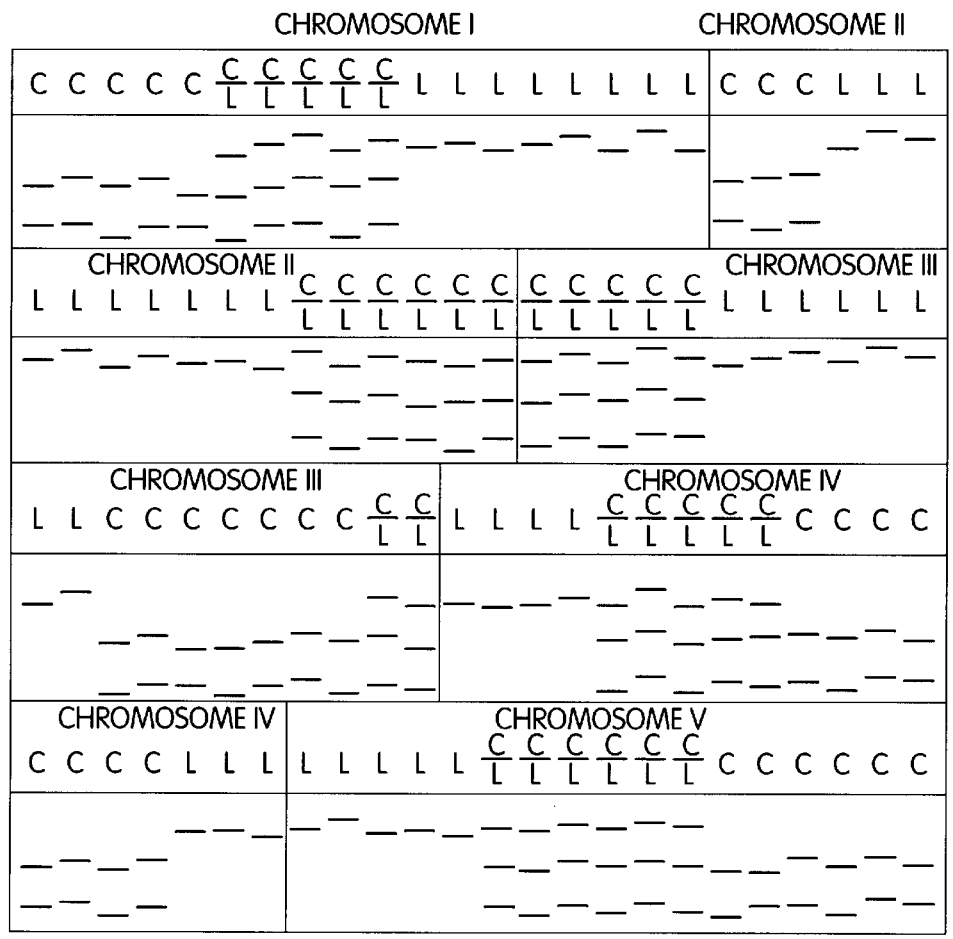
FIG. 8 is a schematic of a typical gel analysis according the method described in FIG. 7.
Figure 9A:
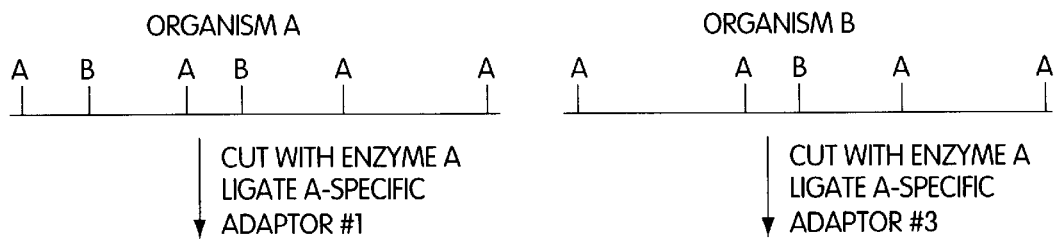
FIGS. 9A–E are schematics of a method for cloning polymorphic restriction fragments.
Figure 9B:
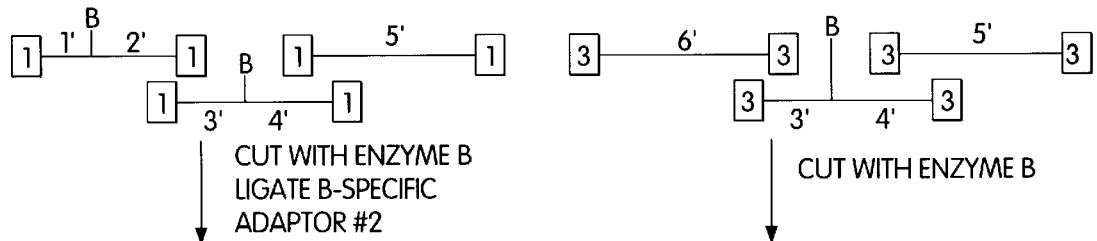
Figure 9C:
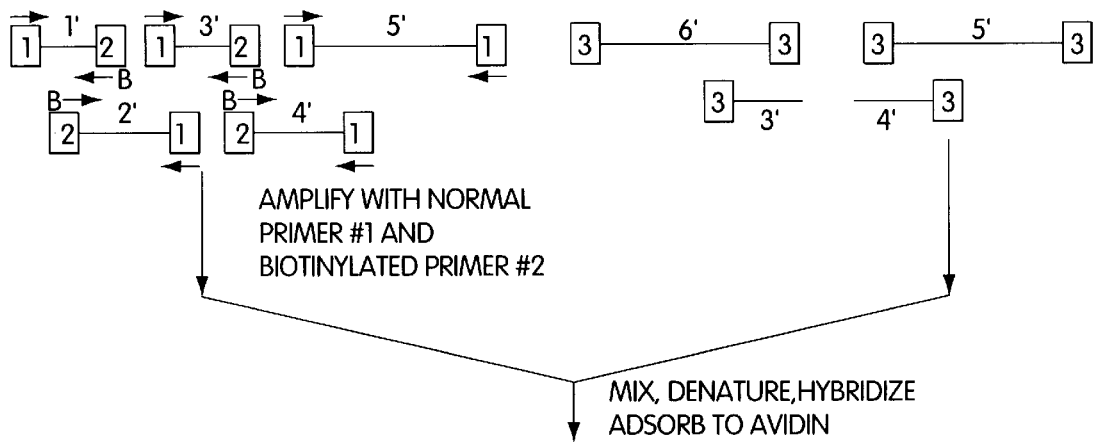
Figure 9D:
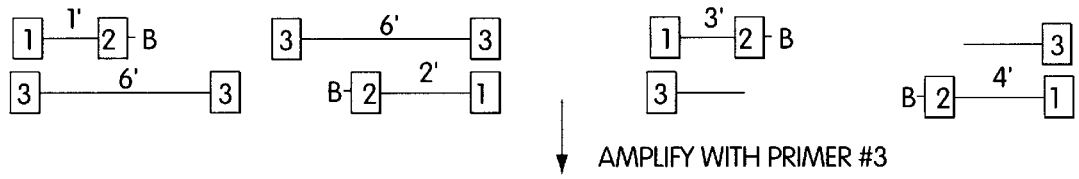
Figure 9E:
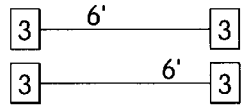

In a preferred method of carrying out this method, sets of primer pairs are provided that detect a number of RFLP markers. Each set of primers may be provided, for example, in one of the wells of a 96-well microtiter plate, and PCR reactions run independently. Following restriction digestion, the reaction products are transferred to an agarose gel and separated by electrophoresis. A typical result of this method is shown in FIG. 8.

Detection of the amplified and cleaved products after electrophoretic separation can be carried out by standard methods of DNA staining (e.g., ethidium bromide staining) or blotting (e.g., Southern blotting). Alternatively, one or both of the PCR primers can be detectably labeled, and the labels can be detected as described above.

Example X.

A preferred use of the methods of the invention is in conjunction with a method called RFLP subtraction. RFLP subtraction provides a large number of polymorphic genetic markers, while the methods of the present invention provide efficient methods for their analysis.

Carrying out RFLP subtraction results in the purification of fragments that are present in one population (the tracer) but absent in another (the driver). Purification is achieved by removing all of the fragments in the tracer DNA that have counterparts in the driver DNA using subtractive hybridization (Innis et al., PCR Protocols: A Guide to Methods and Applications, Academic Press, Harcourt Brace Javanovich, New York, 1990). In RFLP subtraction, the tracer is a size fraction of digested DNA from one strain and the driver is the same size fraction from a polymorphic strain. The products obtained after removing the common sequences are RFLPs; they are sized tracer fragments whose driver counterparts are not found in the same size fraction.

There are three steps in RFLP subtraction: preparation of the driver and tracer, subtractive hybridization, and removal of non-hybridizing sequences from the tracer. To prepare the driver and tracer DNA, genomic DNA from two different strains is digested with a restriction endonuclease, and the ends of the restriction fragments from each strain are capped with different oligonucleotide adapters. The low molecular weight fragments are then purified from a slice of an agarose gel and amplified using one of the adapter strands as a PCR primer. A biotinylated primer can be used to amplify the driver so that driver DNA can be removed following the subtractive hybridizations by binding to avidin coated beads.

Three rounds of subtractive hybridization are performed to remove tracer sequences that also occur in the driver. A small amount of tracer is mixed with an excess of biotinylated driver, the mixture is denatured and allowed to re-anneal. Most tracer sequences will hybridize to complementary biotinylated driver strands. Some tracer sequences, however, are not represented in the driver because they reside on large restriction fragments (i.e., they are RFLPs) or are missing from the driver genome. These fragments will have no complementary biotinylated strands with which to anneal. The biotinylated driver DNA, and any tracer that has annealed to it, is then removed using avidin-coated beads. The unbound fraction is then subjected to two more rounds of subtractive hybridization, tracer DNA remaining after the third round is amplified, and poorly hybridizing sequences are removed.

Example XI.

FIGS. 9A–9E show a preferred method for cloning polymorphic restriction fragments. The object of this method is to clone restriction fragments from organism B (generated by restriction endonuclease A) that do not contain cleavage sites for restriction endonuclease B, and which correspond to restriction fragments in organism A (generated by restriction endonuclease A) that do contain at least one restriction site for restriction endonuclease B. These polymorphic restriction fragments are useful as CAPS markers for the detection methods described above.

Referring to the method outlined in FIGS. 9A–9E, in step A, genomic DNA isolated from polymorphic individuals A and B is separately digested with restriction enzyme A, which preferably leaves so-called sticky ends. An oligonucleotide adaptor (#1), with complementary sticky ends, is ligated to the restriction fragments from individual A. A different oligonucleotide adaptor (#3) is ligated to the restriction fragments from individual B.

In step B, the restriction fragments from step A are cleaved with restriction endonuclease B, which again preferably leaves sticky ends. In the case of the DNA fragments from individual A, an oligonucleotide adaptor (#2), with complementary sticky ends for enzyme B, is ligated to the restriction fragments generated by cleavage with enzyme B.

In step C, the DNA fragments from individual A are amplified using the PCR with an oligonucleotide primer complementary to adaptor #1 and with a biotinylated oligonucleotide primer complementary to adaptor #2.

In step D, the amplified products originating from individual A are mixed with the non-amplified fragments of step B from individual B. The mixed DNA fragments are then heat denatured, annealed, and adsorbed onto an avidin-coated solid support (e.g., beads). The avidin coated support containing the adsorbed fragments is thoroughly washed. If desired, the adsorbed fragments may be eluted, re-amplified with the same primers as above, adsorbed onto a fresh avidin-containing support, and thoroughly washed. This step can be repeated as many times as is necessary or desired.

In step E, the fragments adsorbed to the avidin-coated beads are eluted and amplified using PCR with primers complementary to adaptor #3. The amplified products should correspond to the desired restriction fragments described above. These amplified fragments are cloned and then tested individually using the Southern DNA blot hybridization method for their ability to display the desired RFLP.

Example XII.

In this method, the nucleic acid is amplified by PCR using a first and a second primer flanking the polymorphic restriction site, with the first primer being tagged with a detectable label. The amplification generates a PCR product containing a first strand tagged with the detectable label and a second, unlabeled strand. The PCR product is digested with the restriction endonuclease corresponding to the polymorphic restriction site and the digestion product is denatured. The denatured product is contacted with a first probe that (1) contains a sequence that hybridizes to a first sequence in the first strand of the PCR product, and (2) is immobilized on a first binding element. The first sequence is between the polymorphic restriction site and the sequence in the first strand that is complementary to the second primer.

The first binding element is monitored for the presence of the detectable label. Detection of the detectable label on the first binding element indicates the absence of the polymorphic restriction site in the nucleic acid, and a failure to detect the detectable label on the first binding element indicates the presence of the polymorphic restriction site in the nucleic acid.

In addition to the first probe described above, this method can employ the use of a second, a third, or a fourth probe. The second probe contains a sequence that hybridizes to a second sequence which is in the first strand and is between the polymorphic restriction site and the sequence in the first strand that corresponds to the first primer. The third probe contains a sequence that hybridizes to a third sequence which is in the second strand and is between the polymorphic restriction site and the sequence in the second strand corresponding to the second primer. The fourth probe contains a sequence that hybridizes to a fourth sequence which is in the second strand and is between the polymorphic restriction site and the sequence in the second strand that is complementary to the first primer. The second, third, and fourth probes are immobilized on a second, third, and fourth binding element, respectively. The second binding element can be monitored for the presence of the detectable label as a positive control, while the third or fourth binding elements can be monitored for the presence of the detectable label as negative controls. The first, second, third, and fourth binding elements, in this and in other methods of the invention, can be present on a solid support having similar sets of binding elements for testing different nucleic acids (see, for example, FIG. 11).

The binding elements, for example, the first, second, third, and fourth binding elements, used in this method of the invention can be present as distinct regions on a single solid support. For example, they can be specific sets of nucleic acids bound to distinct regions on a glass plate or on a microchip, such as a glass, silicon, or glass-silicon microchip (see above).

Example XIII.

In this method a nucleic acid is amplified by PCR using a first and a second primer flanking the polymorphic restriction site. The first primer is tagged with a first detectable label and the second primer is tagged with a second detectable label. The amplification thus generates a PCR product containing a first strand tagged with the first detectable label and a second strand tagged with the second detectable label. In this method, the first and second labels can be identical or distinct.

The PCR product is treated with a restriction endonuclease corresponding to the polymorphic restriction site to generate a digestion product, which is denatured to generate a denatured product. The denatured product is contacted with a first and a second probe. The first probe, which is immobilized on a first binding element, contains a sequence that hybridizes to a first sequence in the first strand that is between the polymorphic restriction site and the sequence in the first strand that is complementary to the second primer. The second probe, which is immobilized on a second binding element, contains a sequence that hybridizes to a second sequence in the second strand that is between the polymorphic restriction site and the sequence in the second strand that is complementary to the first primer.

The first binding element is monitored for the presence of the first detectable label and the second binding element is monitored for the presence of the second detectable label. Detection of the first detectable label on the first binding element and detection of the second detectable label on the second binding element indicates the absence of the polymorphic restriction site in the nucleic acid, while a failure to detect the first detectable label on the first binding element and a failure to detect the second detectable label on the second binding element indicates the presence of the polymorphic restriction site in the nucleic acid.

In addition to the first and second probes described above, this method can involve the use of a third and fourth probe. The third probe, which is immobilized on a third binding element, contains a sequence that hybridizes to a third sequence which is in the first strand and that is between the polymorphic restriction site and the sequence in the first strand corresponding to the first primer. The fourth probe, which is immobilized on a fourth binding element, contains a sequence that hybridizes to a fourth sequence which is in the second strand and that is between the polymorphic restriction site and the sequence in the second strand corresponding to the second primer.

The third or fourth binding elements can be monitored for the presence of the first or second detectable labels as controls. For example, the third binding element can be monitored for the presence of the first detectable label and the fourth binding element can be monitored for the presence of the second detectable label.

Figure 10:
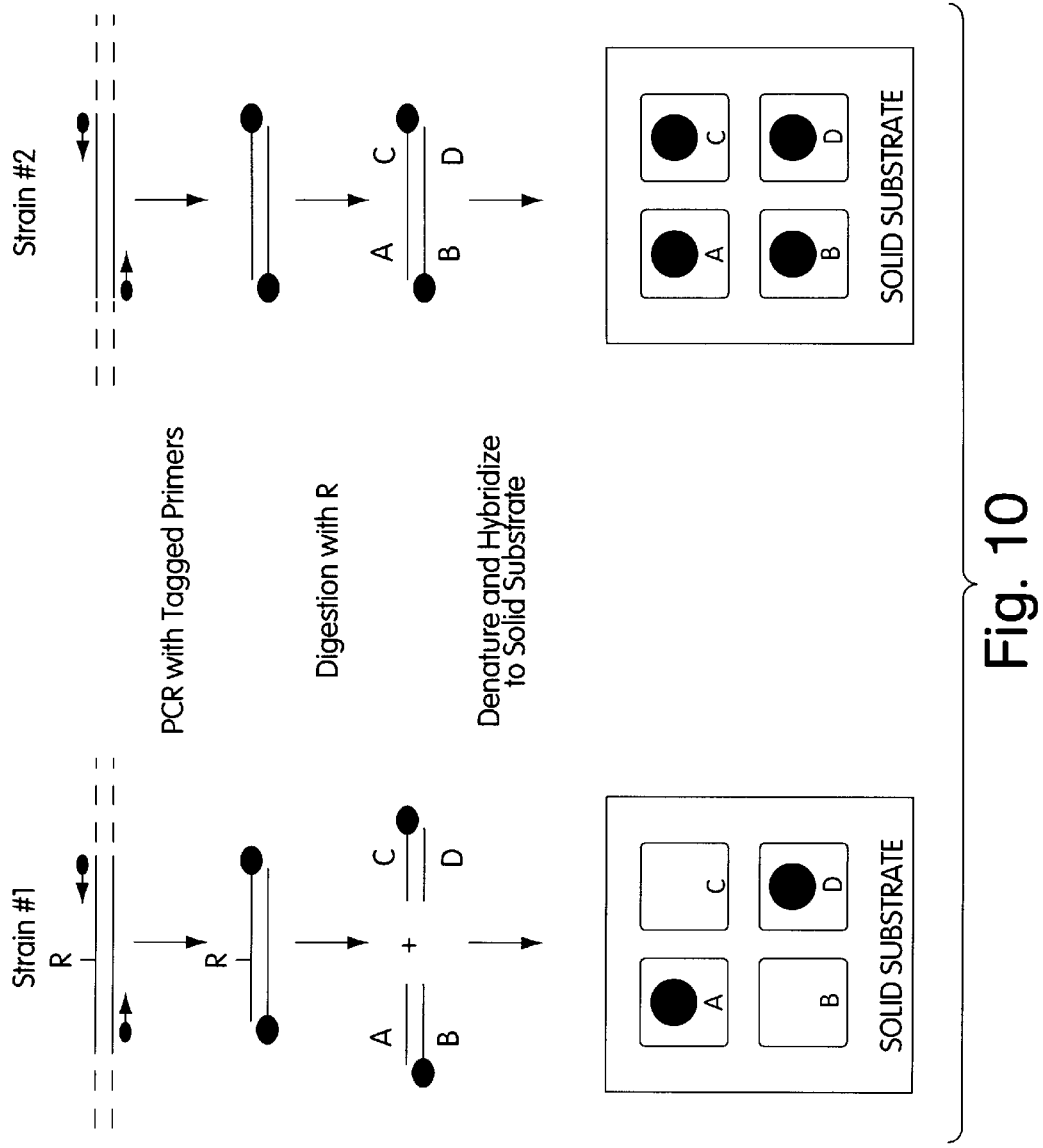
FIG. 10 is a schematic of a non-gel based method for detection of CAPS markers.
Figure 11:
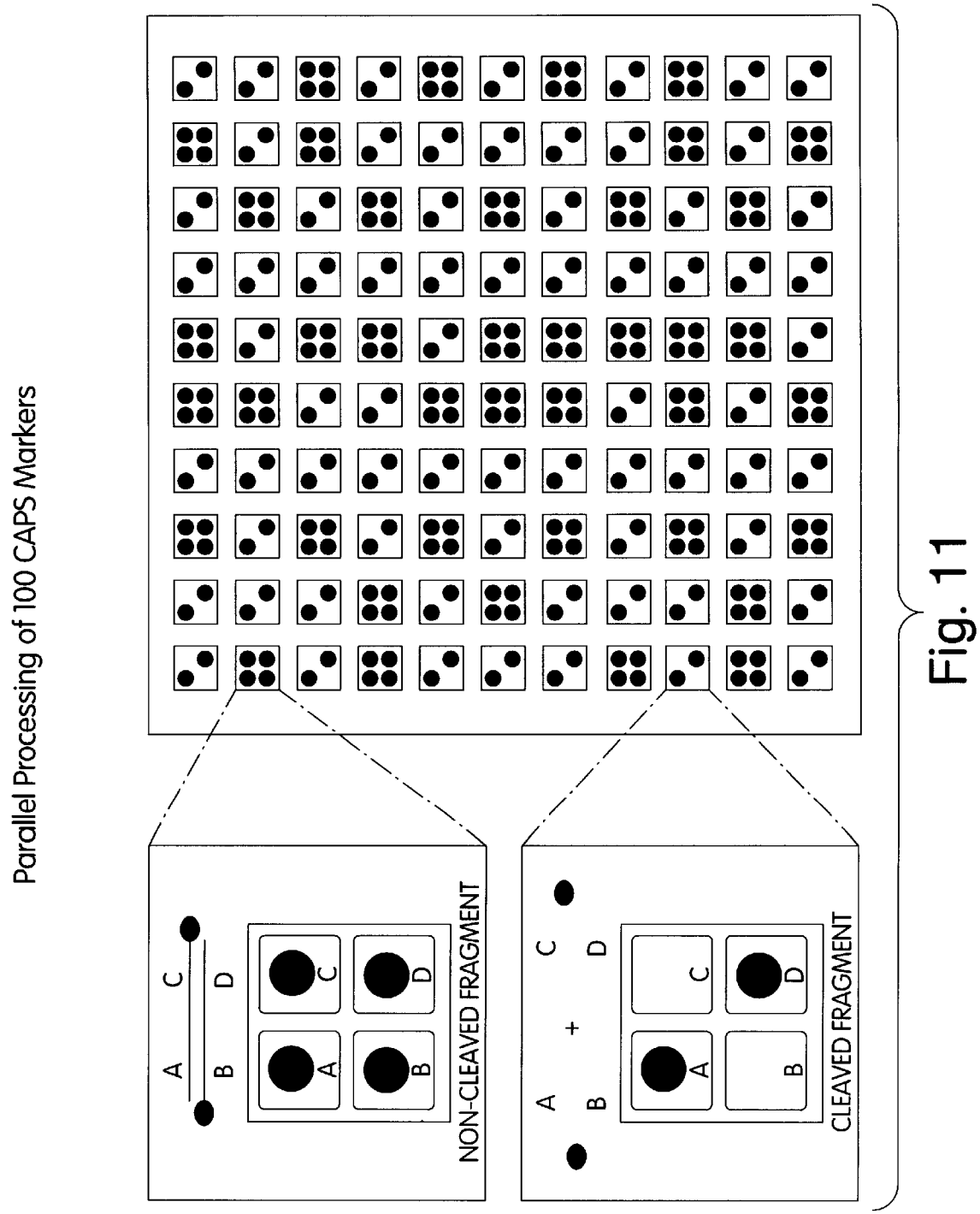
FIG. 11 is a schematic of parallel processing of 100 CAPS markers on a microchip containing an array of oligonucleotide probes.

The first and second, or the first, second, third, and fourth binding elements can be present as distinct regions on a solid support, such as glass (e.g., a glass plate) or a microchip (e.g., a silicon or a silicon-glass microchip). Embodiments of this method are illustrated in FIGS. 10 and 11.

Example XIV.

In this method, the nucleic acid is amplified by PCR using a first and a second primer flanking the polymorphic restriction site. The amplification generates a PCR product containing a first strand containing a sequence corresponding to the first primer and a second strand containing a sequence corresponding to the second primer.

The PCR product is treated with a restriction endonuclease corresponding to the polymorphic restriction site to generate a digestion product, which is denatured to generate a denatured product. The denatured product is contacted with an oligonucleotide to generate a first reaction product. The oligonucleotide contains a 3' portion that hybridizes to a first region in the first strand that flanks the polymorphic restriction site on the side of the polymorphic restriction site containing a sequence corresponding to the 5' first primer. The 3' end of the oligonucleotide is blocked by, e.g., a di-deoxynucleotide, so that it cannot serve as a primer for DNA polymerase. The oligonucleotide contains a 5' portion that does not hybridize to a second region in the first strand that flanks the polymorphic restriction site on the side of the polymorphic restriction site containing a sequence that is complementary to the second primer. The use of such an oligonucleotide to label a cleaved end of a CAPS marker is illustrated in FIG. 12.

As illustrated in FIG. 12., the first reaction product is treated with a DNA polymerase to extend the unblocked, primed 3' end to generate a second reaction product, which is amplified by PCR using the first primer, tagged with a first detectable label, and a third primer, which hybridizes to a sequence that is complementary to the 5' portion of the oligonucleotide, to generate a second PCR product. The third primer is tagged with a second detectable label. In this method, the first and second detectable labels can be identical or distinct.

The second PCR product is denatured to generate a second denatured product, which is contacted with a first and a second probe. The first probe, which is immobilized on a first binding element, contains a sequence that hybridizes to a first sequence in the second strand that is between the polymorphic restriction site and the sequence in the second strand that is complementary to the first primer. The second probe, which is immobilized on a second binding element, contains a sequence that hybridizes to a second sequence in the first strand that is between the polymorphic restriction site and the sequence in the first strand that is complementary to the second primer.

The first binding element is monitored for the presence of the second detectable label and the second binding element is monitored for the presence of the first detectable label. Detection of the second detectable label on the first binding element and detection of the first detectable label on the second binding element indicates a heterozygote, detection of the second detectable label on the first binding element and a failure to detect the first detectable label on the second binding element indicates a homozygote containing the polymorphic restriction site, and detection of the first detectable label on the second binding element and a failure to detect the second detectable label on the first binding element indicates a homozygote lacking the polymorphic restriction site.

In addition to the first and second probes described above, this method can employ a third or a fourth probe. The third probe, which is immobilized on a third binding element, contains a sequence that hybridizes to a third sequence in the first strand that is between the polymorphic restriction site and the sequence in the first strand corresponding to the first primer. The fourth probe, which is immobilized on a fourth binding element, contains a sequence that hybridizes to a fourth sequence in the second strand that is between the polymorphic restriction site and the sequence in the second strand corresponding to the second primer.

The third or fourth binding elements can be monitored for the presence of the first or second detectable labels as controls. For example, the third binding element can be monitored for the presence of the first detectable label.

The first and second, or the first, second, third, and fourth binding elements can be present as distinct regions on a solid support, such as a glass (e.g., a glass plate) or silicon (e.g., a microchip) support.

Figure 13:
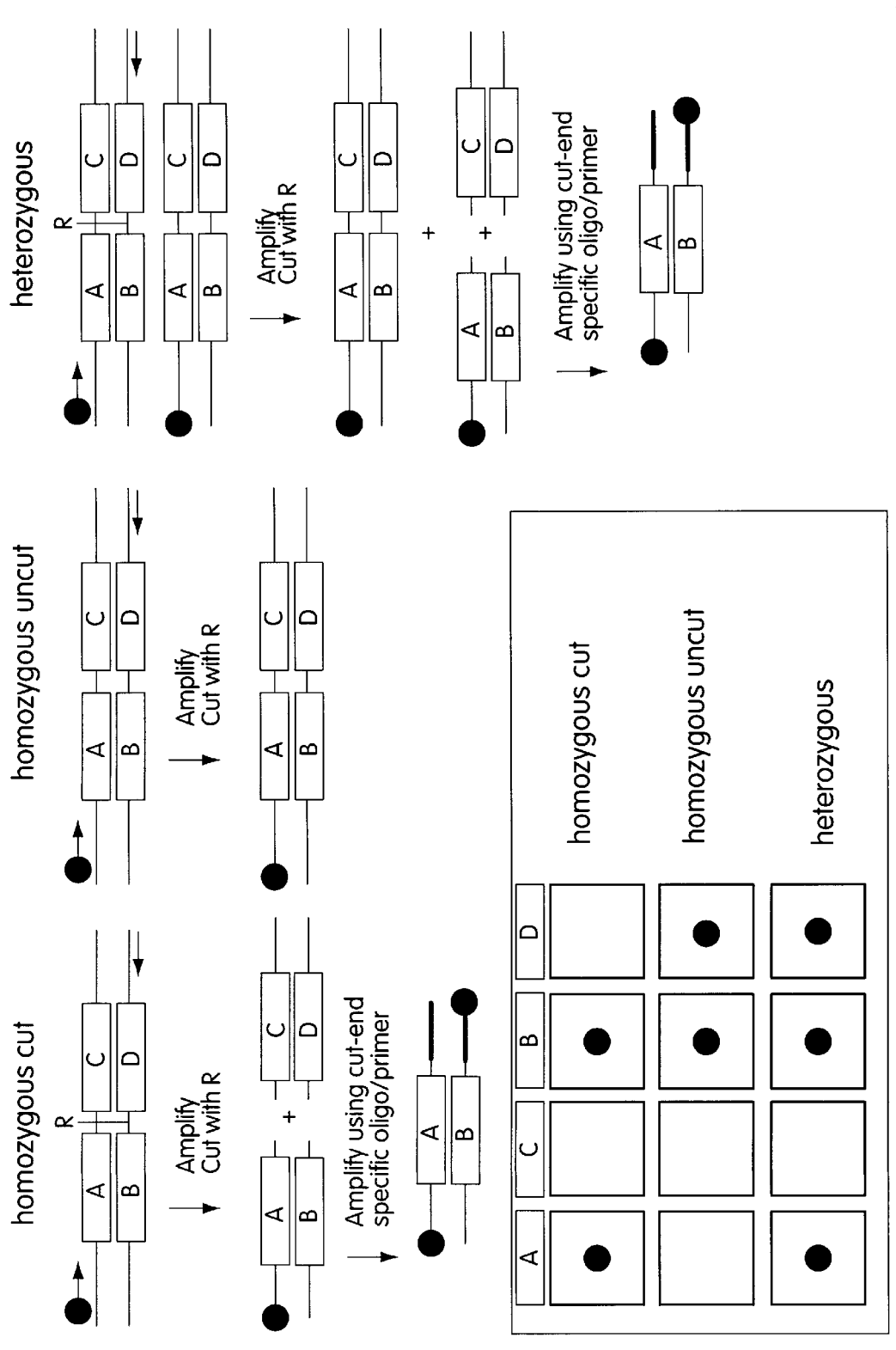
FIG. 13 is a schematic of a method for distinguishing heterozygous CAPS alleles from homozygous CAPS alleles, involving the use of the method for detecting a cleaved end of a CAPS marker shown in FIG. 12.

This embodiment is illustrated in FIG. 13.

Use of oligonucleotides as described above provides several advantages. For example, because there can be a significant amount of overlap between the oligonucleotide and the cleaved product, highly stringent conditions can be used in the annealing reaction, leading to increased specificity. In addition, the 5' end of the oligonucleotide can be the same for many CAPS markers, as it is by design not homologous to any amplified sequences corresponding to a CAPS marker for an organism of interest. These advantages also apply to other methods employing such an oligonucleotide, as are described below.

Example XV.

The method described in this example can be used to detect polymorphisms, for example, single nucleotide polymorphisms (SNPs). The method involves the use of oligonucleotide primers that modify the sequence flanking the polymorphic nucleotide site to generate a new sequence that can be cleaved by a restriction endonuclease, in such a way that the products can be readily assayed in a high-throughput manner by hybridization to probes having complementary sequences and that are immobilized on solid supports. The SNP is modified using PCR such that the PCR products corresponding to the two different SNP alleles can be cut with restriction endonucleases. In one embodiment, a single endonuclease is used to cut the modified, amplified fragment derived from one allele, but not the modified, amplified fragment derived from the other allele. In another embodiment, a single restriction endonuclease is used to cut the modified, amplified fragments derived from both alleles. And, in yet other embodiments, two or more endonucleases are utilized, each specifically cleaving one of the modified, amplified fragments derived from one of the two alleles, but not the other amplified fragment from the other allele.

The method also involves the use of separate and sequential PCR reactions using Taq polymerase (which lacks exonuclease proofreading activity) to incorporate each single nucleotide change, where the changes occur within 4 nucleotides of one another on the same strand of DNA. For example, to convert a four base sequence into a restriction site that requires two changes, two sequential PCR reactions are carried out to incorporate each of these two changes. This approach guarantees that the final PCR product will have the desired nucleotide modifications. It will be understood that thermostable DNA polymerases other than Taq polymerase can also be used in the PCR reactions of this method, provided that the thermostable DNA polymerase used lacks an exonuclease proofreading activity.

In a variant of the method, for the creation of a restriction endonuclease recognition site that requires two nucleotide changes and where the nucleotides to be changed are separated by at least six nucleotides on the same strand of DNA, the two changes can be introduced during one PCR amplification reaction. This technique may be used, for example, to create the recognition site for the BslI restriction endonuclease, particularly for G and C residue modifications. Alternatively, any number of other restriction endonuclease recognition sites may be created, including ones which involve A and T residue modifications. Sites which are useful in the invention include, without limitation, sites corresponding to the PacI, BsaBI, EcoNI, and DrdI restriction endonucleases.

Different PCR primers are used in separate (e.g., parallel) PCR reactions corresponding to each of the two SNP alleles. The method also can involve the incorporation of so-called "tag" sequences and universal primer binding sites into the primer designs. These sequences allow the PCR products to be readily labeled and also facilitate products corresponding to each allele to be distinguished by hybridization to complementary DNA sequences immobilized on a solid support.

FIGS. 14A, 14B, 15A, 15B, and 16 are schematic diagrams showing one example of how the method can be applied to the detection of specific SNPs that exist in the species Arabidopsis thaliana to distinguish the ecotypes Columbia and Landsberg erecta. FIGS. 14A and 14B illustrate the method by which PCR products that correspond to an SNP (the third bold base pair from the left, GC, in FIG. 14A and the second bold base pair from the left, AT, in FIG. 14B, that are not located within a cleavage site for a restriction endonuclease) can be modified from the original sequence in such a way that they can be detected by cleavage using two different restriction enzymes (HhaI in FIG. 14A or DpnII in FIG. 14B). These modifications occur within the distance which characterizes a restriction site, typically, 15 nucleotides. As shown in these Figures, the cleavage events depend on the SNP alleles.

In FIG. 14A, mPr1 is an oligonucleotide primer that contains a single mismatch relative to the template sequence (that is, the G residue two nucleotides from the 3' end). The first nucleotide incorporated in the polymerization reaction corresponds to the SNP. rPr1 signifies the reverse primer corresponding to mPr1 and is complementary to a sequence in the template DNA strand that is positioned, preferably, at least 15 nucleotides (typically 50–500 nucleotides) from the SNP. This reverse primer can be placed a significant distance from the SNP to avoid the product of the first PCR reaction serving as a primer in the second PCR reaction. mPr2 in FIG. 14A signifies an oligonucleotide primer that contains at least three important elements. First, mPr2 contains a sequence proximal to the 5' end of the primer that serves as a "forward" universal priming site (e.g., the sequence of the phage T3 binding site for RNA polymerase). Second, in the middle of the primer, mPr2 contains a so-called unique "tag" sequence composed of approximately 20 nucleotide residues that does not have a corresponding sequence in the target DNA and that serves to bind the PCR product to a complementary sequence immobilized on a solid support. The length of the tag sequence can be varied as required depending on the method used to detect the PCR product. And third, mPr2 contains a sequence proximal to the 3' end of the primer that is approximately 17–21 nucleotide residues in length, that corresponds to the sequence flanking the SNP, and that contains a single nucleotide mismatch with the template DNA (for example, the G residue at the 3' end of the primer indicated in bold in FIG. 14A).

rPr2 in FIG. 14A signifies an oligonucleotide primer that also contains at least three important elements. First, rPr2 contains a sequence proximal to the 5' end of the rPr2 primer that serves as a "reverse" universal priming site (e.g., the sequence of the phage T7 binding site for RNA polymerase). Second, in the middle of the primer, rPr2 contains a "tag" sequence composed of approximately 20 nucleotide residues that does not have a corresponding sequence in the target DNA and that serves to bind the PCR product to a complementary sequence immobilized on a solid support. Again, the length of the tag sequence can be varied as required depending on the method used to detect the PCR product. And third, rPr2 contains a sequence proximal to the 3' end of the primer that is approximately 17–21 nucleotide residues in length and that corresponds to the sequence flanking the SNP.

FIG. 14B can be described in a manner similar to FIG. 14A. In particular, primers mPr3 and rPr3 have properties similar to mPr1 and rPr1, respectively, and primers mPr4 and rPr4 have properties similar to mPr2 and rPr2, respectively.

FIGS. 15A and 15B illustrate how the products generated in FIGS. 14A and 14B can be labeled by utilizing, for example, a fluorescently labeled universal primer to amplify and thereby label the product of the second PCR reaction. A key feature of this labeling procedure is that the PCR product generated using the primers designed to generate the DpnII and HhaI sites, respectively, are differentially labeled on opposing strands. That is, in one labeling PCR reaction, a fluorescently labeled forward universal primer is used in combination with an unlabeled reverse universal primer. In the other labeling reaction, the reverse universal primer is labeled using, for example, a detectably labeled primer that specifically hybridizes to the reverse universal primer in a PCR reaction with an un1 labeled corresponding forward primer.

Following incorporation of the label to generate detectably labeled PCR products, the products are cleaved with the corresponding restriction endonuclease (for example, HhaI or DpnII), and the cleaved products are then hybridized to a solid support containing sequences complementary to the tag sites. In FIGS. 15A and 15B, Tags 1 and 4 are incorporated into the PCR primers and Tags 2 and 3 are generated during the course of the PCR reaction. In the bottom of FIGS. 15A and 15B, the numbers in the representation of the solid support represent nucleotide sequences complementary only to the nucleotide tags in the PCR products. That is, for example, Tag sequence 1 on the support hybridizes to and therefore "captures" Tag sequence 3 in the PCR product. In one particular example, in FIG. 15B, the DpnII restriction endonuclease recognition site is created only in the Columbia allele. Hence, the label is incorporated only in the sequence tagged with Tag sequence 4, and it hybridizes to Tag 2 on the solid support. In contrast, in the Landsberg allele, the labeled PCR product is not cleaved by exposure to DpnII; therefore sequences tagged with both Tag 3 and Tag 4 include the label, and the label hybridizes to both Tag 1 and Tag 2 on the solid support. By this means, the presence of a Columbia allele is readily determined.

The present method for detecting SNPs is referred to "CAMPS" for Cleaved Amplified Modified Polymorphic Sequences. FIG. 16 illustrates that CAMPS markers are "co-dominant." That is, CAMPS markers can be used to determine whether an individual is homozygous or heterozygous for a particular SNP. In the particular example shown in FIG. 16, a DpnII restriction endonuclease recognition site is incorporated into the Columbia allele, and a HhaI restriction endonuclease recognition site is incorporated into the Landsberg allele. By assaying DNA using the CAMPS technique and the restriction endonucleases DpnII and HhaI, an individual may be characterized as homozygous for Landsberg, homozygous for Columbia, or heterozygous for both alleles.

Figure 17:
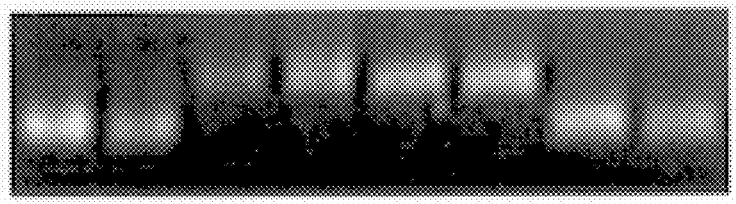
FIG. 17 is a photograph of an agarose gel demonstrating the assay of CAMPS markers by gel electrophoresis. As shown, differences in electrophoretic mobility demonstrate that Columbia DNA ("Col") converted with DpnII primers was digested with DpnII, but this same DNA converted with HhaI primers was not digested with HhaI. Conversely, Landsberg DNA ("La") converted with DpnII primers was not digested with DpnII, but, when converted with HhaI primers, was digested with HhaI.

Although FIGS. 15A, 15B, and 16 demonstrate how the CAMPS assay may be read using a rapid high-throughput solid support-based assay, FIG. 17 illustrates how CAMPS markers can be assayed by agarose gel electrophoresis. DNA from *Arabidopsis thaliana* ecotypes Landsberg and Columbia was amplified with either HhaI or DpnII specific primers, as shown in FIGS. 14A, 14B, 15A, and 15B. The final products of the amplification were digested with either HhaI or DpnII, respectively. In the example shown in FIG. 17, the Columbia DNA is converted to contain a DpnII site, and the converted DNA is digested following incubation with DpnII. The Landsberg DNA converted to contain a HhaI site is successfully digested with HhaI.

Figure 18:
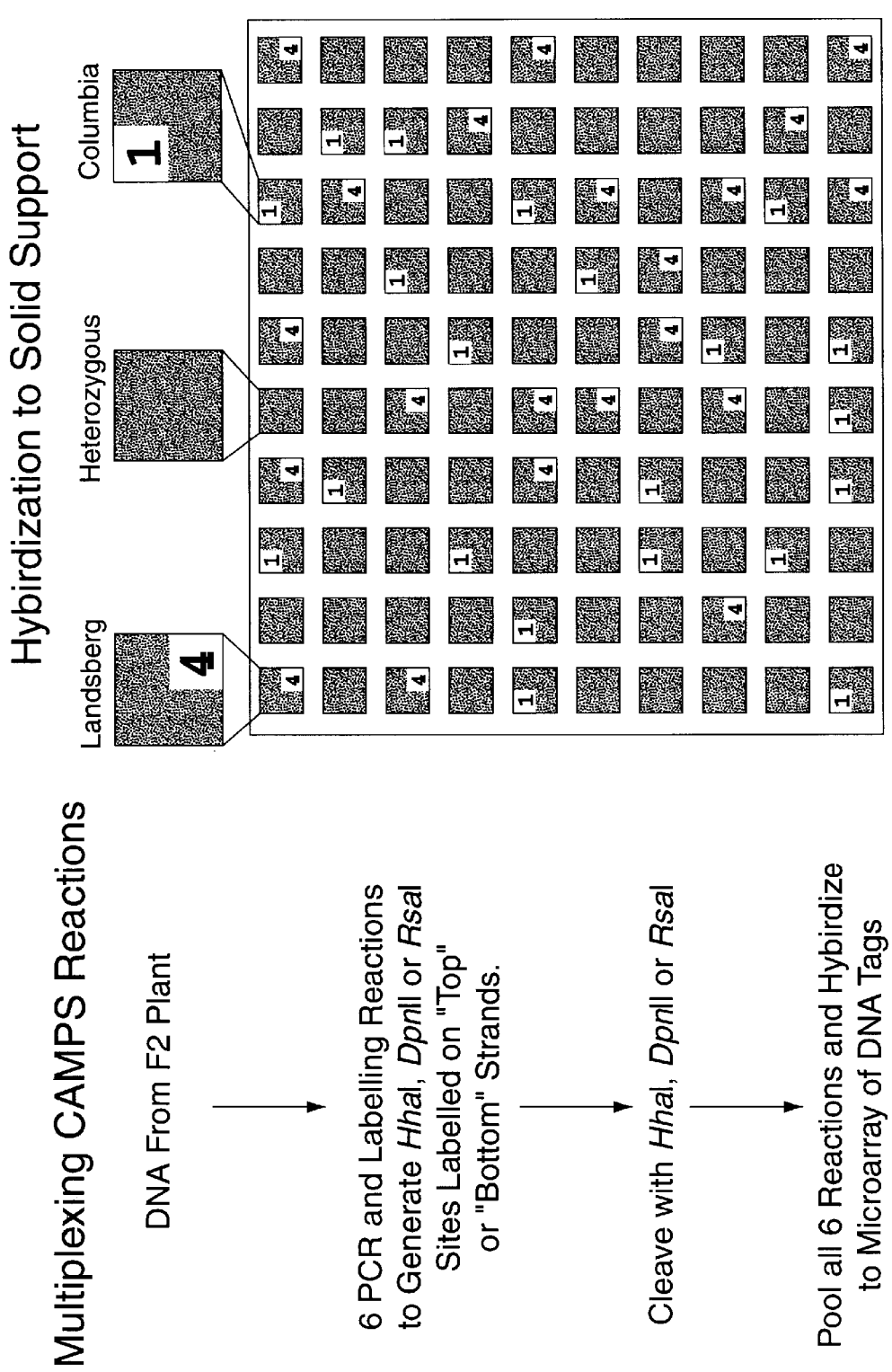
FIG. 18 is a schematic illustrating an exemplary application of the CAMPS method using a solid support microarray of DNA tags.

For use in either technique, the conversion of a polymorphism to a CAMPS marker may be readily accomplished. For example, to distinguish the Columbia and Landsberg alleles in *Arabidopsis thaliana*, we examined 119 polymorphic loci to determine how many could be converted into CAMPS markers. We found that 96 of these 119 polymorphic loci (corresponding to 258 SNPs) could be converted to CAMPS markers (that is, both alleles could be converted) and that these markers could be cleaved by a restriction endonuclease chosen from DpnII, HhaI, or RsaI, using at most 2 successive PCR reactions involving one nucleotide modification per reaction. It will be understood that any number of conversions can be accomplished by simply increasing the number of restriction endonuclease sites created. With respect to the CAMPS detection method illustrated in FIGS. 15A, 15B, and 16, the conversion to CAMPS markers using only three different restriction endonucleases meant that all 96 SNPs could be assayed using PCR amplification and labeling reactions in at most six different test tubes and one hybridization reaction to a single solid support containing 384 corresponding tags (i.e., 4×96= 384). By this method, multiplex PCR reactions may be carried out in which many primer pairs amplify target sequences simultaneously. The reason that six tubes (two corresponding to each restriction endonuclease) are required, rather than three tubes (one corresponding to each restriction endonuclease), is that some CAMPS markers that correspond to a specific restriction endonuclease need to be labeled on the "top" strand (forward universal primer labeled) whereas other markers corresponding to the same restriction endonuclease need to be labeled on the "bottom" strand (reverse universal primer labeled). An exemplary CAMPS assay using the three restriction endonucleases RsaI, DpnII, and HhaI in conjunction with a solid support carrying a microarray of DNA tags is depicted in FIG. 18. As illustrated by this Figure, the CAMPS technique is readily adaptable to a high through-put assay format.

Other Embodiments

The techniques described herein may be used in any appropriate context, although genetic mapping represents a particularly useful application of the method. In addition, the present methods find use in any number of organisms (including plants and animals).

All publications cited herein are incorporated by reference in their entirety.

Other embodiments are in the claims.

What is claimed is:

1. A method for detecting the presence or absence of a single nucleotide polymorphism in a nucleic acid molecule, said method comprising the steps of:
   (a) providing a nucleic acid molecule comprising a first strand, a second strand, and a nucleotide position suspected of comprising a polymorphism;
   (b) amplifying a portion of said nucleic acid molecule by PCR using a first primer and a second primer, wherein (i) said first primer comprises a 3' region that is complementary to a first region of said first strand, the 5' end of said first region being positioned within 15 nucleotides 3' of said nucleotide position, and said 3' region of said first primer comprising at least one nucleotide mismatch with said first region within 15 nucleotides of said nucleotide position, (ii) said second primer comprises a 3' region that is complementary to a second region of said second strand, the 5' end of said second region being positioned 3' of said nucleotide position, and (iii) said amplification generates a PCR product comprising at least one point mutation, relative to the sequence of said nucleic acid molecule, that forms a portion of a restriction endonuclease recognition site in the presence of a single polymorphic nucleotide in said nucleotide position;
   (c) labeling one end of one strand of the product of step (b) with a detectable label to generate a labeled PCR product comprising a labeled strand;
   (d) treating said labeled PCR product with a restriction endonuclease that recognizes said restriction endonuclease recognition site to generate a digestion product;
   (e) denaturing and contacting said digestion product with a probe that (i) is complementary to a first segment of said labeled strand that is on the opposite side of said nucleotide position from said detectable label, within said labeled strand, (ii) is not complementary to said labeled strand between said nucleotide position and said detectable label, and (iii) is immobilized to a binding element on a solid support; and
   (f) assaying for said detectable label bound to said binding element, wherein the absence of said label bound to said binding element indicates the presence of said single nucleotide polymorphism in said nucleic acid molecule, and the presence of said label bound to said binding element indicates the absence of said single nucleotide polymorphism in said nucleic acid molecule.

2. The method of claim 1, wherein step (b) further comprises amplifying said PCR product by PCR using a third primer and a fourth primer, wherein (i) said third primer comprises a 3' region that is complementary to a third region of said first strand, the 5' end of said third region being positioned within 15 nucleotides 3' of said nucleotide position, and said 3' region of said third primer comprising an additional nucleotide mismatch with said third region within 15 nucleotides of said nucleotide position, (ii) said fourth primer comprises a 3' region that is complementary to a fourth region of said second strand, the 5' end of said fourth region being positioned 3' of said nucleotide position, and (iii) said amplification generates a PCR product comprising an additional point mutation, relative to the sequence of said nucleic acid molecule, that forms an additional portion of said restriction endonuclease recognition site in the presence of said single nucleotide polymorphism.

3. The method of claim 1, wherein step (b) further comprises amplifying said PCR product by PCR using a third primer and a fourth primer, wherein (i) said third primer comprises a 3' region that is complementary to a third region of said first strand, the 5' end of said third region being positioned 3' of said nucleotide position, (ii) said fourth primer comprises a 3' region that is complementary to a fourth region of said second strand, the 5' end of said fourth region being positioned within 15 nucleotides 3' of said nucleotide position, and said 3' region of said fourth primer comprising an additional nucleotide mismatch with said fourth region within 15 nucleotides of said nucleotide position, and (iii) said amplification generates a PCR product comprising an additional point mutation, relative to the sequence of said nucleic acid molecule, that forms an additional portion of said restriction endonuclease recognition site in the presence of said single nucleotide polymorphism.

4. The method of claim 1, wherein said labeling of said one end of said one strand of said product of step (b) is carried out by amplifying by PCR said product of step (b) using a third primer and a fourth primer, wherein (i) said third primer comprises a 3' region that is complementary to a region of said first strand and that is on the same side of said nucleotide position as said first region of said first strand, (ii) said fourth primer comprises a 3' region that is complementary to a region of said second strand and that is on the same side of said nucleotide position as said second region of said second strand, and (iii) either said third primer or said fourth primer comprises a detectable label.

5. The method of claim 1, wherein said first primer further comprises a tag element that is not complementary to said first strand of said nucleic acid molecule, said tag element being positioned 5' to said 3' region of said first primer.

6. The method of claim 5, wherein said first primer further comprises a binding site for a universal primer for amplification, wherein said binding site is not complementary to said first strand of said nucleic acid molecule and is positioned 5' to said tag element.

7. The method of claim 6, wherein said labeling of said 5' end of said first strand of said product of step (b) is carried out by amplifying by PCR said product of step (b) using a third and a fourth primer, wherein (i) the 3' region of said third primer comprises a region having the sequence of said binding site for said universal primer, and (ii) said fourth primer comprises a 3' region that is complementary to a region of said second strand that is 3' of said nucleotide position.

8. The method of claim 1, wherein said second primer further comprises a tag element that is not complementary to said second strand of said nucleic acid molecule, said tag element being positioned 5' to said 3' region of said second primer.

9. The method of claim 8, wherein said second primer further comprises a binding site for a universal primer for amplification, wherein said binding site is not complemenary to said second strand of said nucleic acid and is positioned 5' to said tag element.

10. The method of claim 9, wherein said labeling of said 5' end of said second strand of said product of step (b) is carried out by amplifying by PCR said product of step (b) using a third and a fourth, wherein (i) the 3' region of said third primer comprises a region having the sequence of said binding site for said universal primer, and (ii) said fourth primer comprises a 3' region that is complementary to a region of said first strand that is 3' of said nucleotide position.

11. The method of claim 2, wherein said third primer further comprises a tag element that is not complementary to said first strand of said nucleic acid molecule and is positioned 5' to said 3' region of said third primer.

12. The method of claim 11, wherein said third primer further comprises a binding site for a universal primer for amplification, wherein said binding site is not complementary to said first strand of said nucleic acid molecule and is positioned 5' to said tag element.

13. The method of claim 12, wherein said labeling of said 5' end of said first strand of said product of step (b) is carried out by amplifying by PCR said product of step (b) using a fifth and a sixth primer, wherein (i) the 3' region of said fifth primer comprises a region having the sequence of said binding site for said universal primer, and (ii) said sixth primer comprises a 3' region that is complementary to a region of said second strand that is 3' of said nucleotide position.

14. The method of claim 2, wherein said fourth primer further comprises a tag element that is not complementary to said second strand of said nucleic acid molecule and is positioned 5' to said 3' region of said fourth primer.

15. The method of claim 14, wherein said fourth primer further comprises a binding site for a universal primer for amplification, wherein said binding site is not complementary to said second strand of said nucleic acid molecule and is positioned 5' to said tag element.

16. The method of claim 15, wherein said labeling of said 5' end of said second strand of said product of step (b) is carried out by amplifying by PCR said product of step (b) using a fifth and a sixth primer, wherein (i) the 3' region of said fifth primer comprises a region having the sequence of said binding site for said universal primer, and (ii) said sixth primer comprises a 3' region that is complementay to a region of said first strand that is 3' of said nucleotide position.

17. The method of claim 3, wherein said third primer further comprises a tag element that is not complementary to said first strand of said nucleic acid molecule and is positioned 5' to said 3' region of said third primer.

18. The method of claim 17, wherein said third primer further comprises a binding site for a universal primer for amplification, wherein said binding site is not complementary to said first strand of said nucleic acid molecule and is positioned 5' to said tag element.

19. The method of claim 18, wherein said labeling of said 5' end of said first strand of said product of step (b) is carried out by amplifying by PCR said product of step (b) using a fifth and a sixth primer, wherein (i) the 3' region of said fifth primer comprises a region having the sequence of said binding site for said universal primer, and (ii) said sixth primer comprises a 3' region that is complementary to a region of said second strand that is 3' of said nucleotide position.

20. The method of claim 3, wherein said fourth primer further comprises a tag element that is not complementary to said second strand of said nucleic acid molecule and is positioned 5' to said 3' region of said fourth primer.

21. The method of claim 20, wherein said fourth primer further comprises a binding site for a universal primer for amplification, wherein said binding site is not complementary to said second strand of said nucleic acid molecule and is positioned 5' to said tag element.

22. The method of claim 21, wherein said labeling of said 5' end of said second strand of said product of step (b) is carried out by amplifying by PCR said product of step (b) using a fifth and sixth primer, wherein (i) the 3' region of said fifth primer comprises a region having the sequence of said binding site for said universal primer, and (ii) said sixth primer comprises a 3' region that is complementary to a region of said first strand that is 3' of said nucleotide position.

23. The method of claim 1, 2, or 3, wherein said first primer further comprises a first tag element that is not complementary to said first strand of said nucleic acid molecule, said first tag element being positioned 5' to said 3' region of said first primer, and said second primer further comprises a second tag element that is not complementary to said second strand of said nucleic acid molecule, said second tag element being positioned 5' to said 3' region of said second primer.

24. The method of claim 23, wherein, upon said amplification, said first tag element creates a third tag element in the complementary strand of said PCR product and said second tag element creates a fourth tag element in the complementary strand of said PCR product.

25. The method of claim 24, wherein said solid support comprises four binding elements to each of which is immobilized a probe that binds one of said first tag element, said second tag element, said third tag element, or said fourth tag element.

26. The method of claim 25, wherein step (f) is carried out by assaying for said detectable label bound to each of said four binding elements.

27. The method of claim 1, 2, or 3, wherein said solid support is a chip.

28. A method for detecting the presence of a first single nucleotide polymorphism or a second single nucleotide polymorphism at a nucleotide position in a nucleic acid molecule, said method comprising the steps of:

(a) providing a first aliquot of a nucleic acid molecule, said nucleic acid molecule comprising a first strand, a second strand, and a nucleotide position suspected of comprising a polymorphism;

(b) amplifying a portion of said nucleic acid molecule by PCR using a first primer and a second primer, wherein (i) said first primer comprises a 3' region that is complementary to a first region of said first strand, the 5' end of said first region being positioned within 15 nucleotides 3' of said nucleotide position, and said 3' region of said first primer comprising at least one nucleotide mismatch with said first region within 15 nucleotides of said nucleotide position, (ii) said second primer comprises a 3' region that is complementary to a second region of said second strand, the 5' end of said second region being positioned 3' of said nucleotide position, and (iii) said amplification generates a first PCR product comprising at least one point mutation, relative to the sequence of said nucleic acid molecule, that forms a portion of a first restriction endonuclease recognition site in the presence of a first single polymorphic nucleotide in said nucleotide position;

(c) labeling one end of one strand of the product of step (b) with a detectable label to generate a first labeled PCR product comprising a labeled strand;

(d) treating said first labeled PCR product with a first restriction endonuclease that recognizes said first restriction endonuclease recognition site to generate a first digestion product;

(e) denaturing and contacting said first digestion product with a first probe that (i) is complementary to a first segment of said labeled strand that is on the opposite side of said nucleotide position from said detectable label, within said labeled strand, (ii) is not complementary to said labeled strand between said nucleotide position and said detectable label, and (iii) is immobilized on a first binding element;

(f) assaying for said detectable label bound to said first binding element;

(g) providing a second aliquot of said nucleic acid molecule;

(h) amplifying a portion of said nucleic acid molecule by PCR using a third primer and a fourth primer, wherein (i) said third primer comprises a 3' region that is complementary to a first region of said first strand, the 5' end of said first region being positioned within 15 nucleotides 3' of said nucleotide position, and said 3' region of said third primer comprising at least one nucleotide mismatch with said first region within 15 nucleotides of said nucleotide position, (ii) said fourth primer comprises a 3' region that is complementary to a second region of said second strand, the 5' end of said second region being positioned 3' of said nucleotide position, and (iii) said amplification generates a second PCR product comprising at least one point mutation, relative to the sequence of said nucleic acid molecule, that forms a portion of a second restriction endonuclease recognition site in the presence of a second single polymorphic nucleotide in said nucleotide position;

(i) labeling one end of one strand of the product of step (h) with a detectable label to generate a second labeled PCR product comprising a labeled strand;

(j) treating said second labeled PCR product with a second restriction endonuclease that recognizes said second restriction endonuclease recognition site to generate a second digestion product;

(k) denaturing and contacting said second digestion product with a second probe that (i) is complementary to a first segment of said labeled strand that is on the opposite side of said nucleotide position from said detectable label, within said labeled strand, (ii) is not complementary to said labeled strand between said nucleotide position and said detectable label, and (iii) is immobilized on a second binding element; and (l) assaying for said detectable label bound to said second binding element, wherein (i) the absence of said label bound to said first binding element indicates the presence of said first single nucleotide polymorphism; (ii) the absence of said label bound to said second binding element indicates the presence of said second single nucleotide polymorphism; and (iii) the absence of said label bound to both of said first binding element and said second binding element indicates the presence of said first single nucleotide polymorphism and said second single nucleotide polymorphism.

29. A kit for detecting the presence or absence of a single nucleotide polymorphism in a nucleic acid molecule comprising:

(a) a first primer and a second primer flanking a nucleotide position suspected of comprising a polymorphism, wherein (i) said first primer comprises a 3' region that is complementary to a first region of a first strand of said nucleic acid molecule, the 5' end of said first region being positioned within 15 nucleotides 3' of said nucleotide position, and said 3' region of said first primer comprising at least one nucleotide mismatch with said first region within 15 nucleotides of said nucleotide position, and (ii) said second primer comprises a 3' region that is complementary to a second region of a second strand of said nucleic acid molecule, the 5' end of said second region being positioned 3' of said nucleotide position, wherein amplifying said nucleic acid molecule using said first primer and said second primer generates a PCR product comprising at least one point mutation, relative to the sequence of said nucleic acid molecule, that forms a portion of a restriction endonuclease recognition site in the presence of a single polymorphic nucleotide in said nucleotide position; and (b) a probe that either (i) is complementary to a first segment of said second strand and that is on the opposite side of said nucleotide position from said first primer and is not complementary to said second strand between said nucleotide position and said first primer, or (ii) is complementary to a first segment of said first strand that is on the opposite side of said nucleotide position from said second primer and is not complementary to said first strand between said nucleotide position and said second primer, said probe being immobilized to a binding element on a solid support.

30. The kit of claim 29, wherein either of said first primer or said second primer is tagged with a detectable label.

31. The kit of claim 30, wherein said kit further comprises means for assaying said detectable label.

32. The kit of claim 29, wherein said kit further comprises a third primer and a fourth primer, wherein (i) said third primer comprises a 3' region that is complementary to a third region of said first strand, the 5' end of said third region being positioned within 15 nucleotides 3' of said nucleotide position, and said 3' region of said third primer comprising an additional nucleotide mismatch with said third region within 15 nucleotides of said nucleotide position, and (ii) said fourth primer comprises a 3' region that is complementary to a fourth region of said second strand, the 5' end of said fourth region being positioned 3' of said nucleotide position, wherein amplifying said nucleic acid molecule using said third primer and said fourth primer generates a PCR product comprising an additional point relative to the sequence of said nucleic acid molecule, that form an additional portion of said restriction endonuclease recognition site in the presence of a single polymorphic nucleotide in said nucleotide position.

33. The kit of claim 29, wherein said kit further comprises a third primer and a fourth primer, wherein (i) said third primer comprises a 3' region that is complementary to a third region of said first strand, the 5' end of said third region being positioned 3' of said nucleotide position, and (ii) said fourth primer comprises a 3' region that is complementary to a fourth region of said second strand, the 5' end of said fourth region being positioned within 15 nucleotides 3' of said nucleotide position, and said 3' region of said fourth primer comprising an additional nucleotide mismatch with said fourth region within 15 nucleotides of said nucleotide position, wherein amplifying said nucleic acid molecule using said third primer and said fourth primer generates a PCR product comprising an additional point mutation, relative to the sequence of said nucleic acid molecule, that forms an additional portion of said restriction endonuclease recognition site in the presence of a single polymorphic nucleotide in said nucleotide position.

34. The kit of claim 32 or 33, wherein either of said third primer or said fourth primer is tagged with a detectable label.

35. The kit of claim 34, wherein said kit further comprises means for assaying said detectable label bound to said binding element.

* * * * *

UNITED STATES PATENT AND TRADEMARK OFFICE
CERTIFICATE OF CORRECTION

PATENT NO. : 6,110,709
DATED : August 29, 2000
INVENTOR(S) : Frederick M. Ausubel and Michael Mindrinos It is certified that error appears in the above-identified patent and that said Letters Patent is hereby corrected as shown below:

Column 6,
Line 57, insert a new paragraph starting with the word "The".

Column 22,
Line 46, replace "Pacd" with -- PacI --.

Column 23,
Line 16, insert a new paragraph starting with the word "mPr2".

Column 24,
Line 2, replace "unl labeled" with -- unlabeled --.
Line 17, insert a new paragraph starting with the word "In".

Column 31,
Line 4, replace "form" with -- forms --.

Signed and Sealed this

Twenty-first Day of May, 2002

JAMES E. ROGAN
*Director of the United States Patent and Trademark Office*

*Attest:*

*Attesting Officer*